(12) United States Patent
Xu et al.

(10) Patent No.: US 9,822,202 B2
(45) Date of Patent: Nov. 21, 2017

(54) POLYMER/COPPER COMBINATION FOR TARGETED CANCER THERAPY

(71) Applicant: University of South Carolina, Columbia, SC (US)

(72) Inventors: Peisheng Xu, Chapin, SC (US); Huacheng He, West Columbia, SC (US)

(73) Assignee: University of South Carolina, Columbia, SC (US)

(*) Notice: Subject to any disclaimer, the term of this patent is extended or adjusted under 35 U.S.C. 154(b) by 0 days.

(21) Appl. No.: 14/887,373

(22) Filed: Oct. 20, 2015

(65) Prior Publication Data

US 2016/0108160 A1 Apr. 21, 2016

Related U.S. Application Data

(60) Provisional application No. 62/122,455, filed on Oct. 21, 2014.

(51) Int. Cl.
*C08F 220/28* (2006.01)
*A61K 31/795* (2006.01)
*A61K 31/00* (2006.01)

(52) U.S. Cl.
CPC .......... *C08F 220/28* (2013.01); *A61K 31/00* (2013.01); *A61K 31/795* (2013.01); *C08F 2220/282* (2013.01)

(58) Field of Classification Search
None
See application file for complete search history.

(56) References Cited

U.S. PATENT DOCUMENTS

| 4,956,188 A | 9/1990 | Anderson |
| 6,096,331 A * | 8/2000 | Desai .............. A23L 1/296 424/422 |
| 2008/0220090 A1* | 9/2008 | Sabin .............. A61K 9/146 424/632 |
| 2014/0112881 A1* | 4/2014 | Thayumanavan .... C08F 220/20 424/78.29 |

OTHER PUBLICATIONS

Chen et al., "Thiol-reactive amphiphilic block copolymer for coating gold nanoparticles with neutral and functionable surface", Polym. Chem., 2014, 5, 2768, published Jan. 27, 2014.*
Butters, et al.; "Addition of drug/s to a chemotherapy regimen for metastatic breast cancer," *Cochrane Database Syst Rev* (2010) 11, CD003368.
Lehar, et al.; "Synergistic drug combinations tend to improve therapeutically relevant selectivity," *Nat Biotech* (2009) 27 (7), pp. 659-666.

(Continued)

*Primary Examiner* — Jianfeng Song
(74) *Attorney, Agent, or Firm* — Dority & Manning, PA

(57) ABSTRACT

Polymer/copper combination that can selectively target and kill cancer cells are described. Materials can include the reaction product of a biocompatible hydrophilic polymer and pyridine-2-thiol containing monomer. The copolymer reaction product can include pyridine-2-thiol side groups pendant to the backbone via a disulfide linkage. The hydrophilic component can form the polymer backbone and/or can form hydrophilic pendant groups off of the backbone. Copper ions can be associated with the copolymer.

10 Claims, 15 Drawing Sheets

(56) References Cited

OTHER PUBLICATIONS

Maeda, et al.; "Tumor vascular permeability and the EPR effect in macromolecular therapeutics: a review," *J. Control Release* (2000), 65 (1-2), pp. 271-284.
Iyer, et al.; "Exploiting the enhanced permeability and retention effect for tumor targeting," *Drug Discovery Today* (2006), 11 (17-18) pp. 812-818.
Fang, et al.; "The EPR effect: Unique features of tumor blood vessels for drug delivery, factors involved, and limitations and augmentation of the effect," *Adv. Drug Deliv. Rev.* (2010) __, pp. __.
Maeda; "Tumor-selective delivery of macromolecular drugs via the EPR effect: background and future prospects," *Bioconjug Chem* (2010), 21 (5), pp. 797-802.
Fang, et al.; "Factors and mechanism of "EPR" effect and the enhanced antitumor effects of macromolecular drugs including SMANCS," *Adv Exp Med Biol* (2003), 519, pp. 29-49.
Davis, et al.; "Nanoparticle therapeutics: an emerging treatment modality for cancer," *Nat Rev Drug Discov* (2008) 7 (9), pp. 771-782.
Pridgen, et al.; "Biodegradable, polymeric nanoparticle delivery systems for cancer therapy," *Nanomedicine (Lond)*(2007) 2 (5), pp. 669-680.
Nie, et al.; "Nanotechnology applications in cancer," *Annu Rev Biomed Eng* (2007) 9, pp. 257-288.
Everts, M.; "Thermal scalpel to target cancer," *Expert Rev Med Devices* (2007) 4 (2), pp. 131-136.
Brannon-Peppas, et al.; "Nanoparticle and targeted systems for cancer therapy," *Adv Drug Deliv Rev* (2004) 56 (11), pp. 1649-1659.
Blanco, et al.; "Multifunctional Micellar Nanomedicine for Cancer Therapy," *Exp. Biol. Med.* (2009) 234 (2), pp. 123-131.
Van Vlerken, et al.; "Augmentation of Therapeutic Efficacy in Drug-Resistant Tumor Models Using Ceramide Coadministration in Temporal-Controlled Polymer-Blend Nanoparticle Delivery Systems," *The AAPS Journal* (2010) 12 (2), pp. 171-180.
Xu, P., et al.; "Anticancer efficacies of cisplatin-releasing pH-responsive nanoparticles," *Biomacromolecules* (2006), 7 (3), pp. 829-835.
Ghosh, et al.; "Simultaneous and Reversible Functionalization of Copolymers for Biological Applications†," *Macromolecules* (2006) 39 (17), pp. 5595-5597.
Xu, et al.; "Intracellular drug delivery by poly(lactic-co-glycolic acid) nanoparticles, revisited," *Mol Pharm* (2009), 6 (1), pp. 190-201.
Xu, et al.; "Targeted charge-reversal nanoparticles for nuclear drug delivery," *Agnew Chem Int Ed Engl* (2007), 46 (26), pp. 4999-5002.
Panté, et al.; "Nuclear Pore Complex Is Able to Transport Macromolecules with Diameters of ~39 nm," *Molecular Biology of the Cell* (2002) 13 (2), pp. 425-434.
Na, et al.; "Combination antitumor effects of micelle-loaded anticancer drugs in a CT-26 murine colorectal carcinoma model," *International Journal of Pharmaceutics* (2010) 383 (1-2), pp. 192-200.
Chou, T.; "Drug Combination Studies and Their Synergy Quantification Using the Chou-Talalay Method," *Cancer Research* (2010) 70 (2), pp. 440-446.
Liu, et al.; "Direct Syntheses of Pyridyl Disulfide-Terminated Polymers by RAFT Polymerization," *Macromolecular Rapid Communications* (2007) 28(3), pp. 305-314.

\* cited by examiner

POLYMER/COPPER COMBINATION FOR TARGETED CANCER THERAPY

CROSS REFERENCE TO RELATED APPLICATION

The present application claims priority to U.S. Provisional Patent Application Ser. No. 62/122,455 titled "Polymer/Copper Combination For Cancer Targeted Therapy" of Xu, et al. filed on Oct. 21, 2014, the disclosure of which is incorporated by reference herein.

STATEMENT REGARDING FEDERALLY SPONSORED RESEARCH OR DEVELOPMENT

This invention was made with government support under Grant Nos. 5P20GM109091-02 and 1R15CA188847-01A1 awarded by the National Institutes of Health. The government has certain rights in the invention.

BACKGROUND

Although various anticancer drugs have been developed in an attempt to conquer cancer, a large number of cancer patients ultimately still lose their battle. There are two major causes for this failure: inherited or acquired drug resistance by the cancer cells and side effects due to the poor cell selectivity of anticancer drugs. Multidrug resistance allows cancer cells to survive after receiving the original effective drug, which results in the recurrence of the cancer. Selectivity of anticancer drugs predominantly relies on the proliferation rate difference between normal cells and cancer cells as most cancer cells are fast growing. Unfortunately, many normal cells including cells in the digestive tract, bone marrow, hair follicles, and reproductive system are also fast growing and as such vulnerable to anticancer drugs that target quick proliferating cells. Side effects of anticancer drugs can also compromise the function of the heart, nervous system, and kidneys.

To increase the selectivity of anticancer drugs, various approaches have been explored, including utilizing expression level difference of specific receptors on normal and cancer cells as well as focus on unique physiological properties of tumors such as low pH, high glutathione (GSH) levels, and abnormal metal ion concentrations. Recently, high copper concentration levels in tumors have attracted interest. Copper is an important trace metal that plays critical roles in maintaining normal biological functions. Elevated copper concentration (up to 2-3 fold) is frequently observed in a wide spectrum of tumors including ovarian, breast, cervical, prostate and leukemia and is understood to facilitate tumor angiogenesis. Depletion of copper levels in tumors by use of copper chelators such as D-penicillamine, trientine, and disulfiram has been effective in inhibiting angiogenesis and killing cancer cells both in vitro and in vivo. Unfortunately, due to the non-specific tissue distribution and rapid clearance of the chelators, little or no overall benefit has been observed in those trials.

What are needed in the art are materials and methods that can effectively eradiate cancer cells without damaging healthy tissue.

SUMMARY

Objects and advantages of the invention will be set forth in part in the following description, or may be obvious from the description, or may be learned through practice of the invention.

According one embodiment, a polymer/copper combination is disclosed. The polymer/copper combination can include a biocompatible copolymer that includes pyridine-2-thiol side groups pendant to a backbone via a disulfide linkage and also includes copper ions. The biocompatible copolymer also includes a hydrophilic component. The polymer/copper combination also includes copper ions associated with the copolymer. The polymer/copper combination can be in the form of a particle, e.g., a nanoparticle, with the hydrophilic component at the exterior surface of the particle. Optionally, the copolymer can include additional side groups that in one embodiment can also associate with copper ions. For instance, the copolymer can also include a side group pendant to the backbone via a disulfide linkage that can include polyhydroxy functionality that can provide further copper associating capability to the copolymer.

Also disclosed are methods for decreasing the viability of cancer cells by use of the polymer/copper combination. For instance, a method can include delivering the material to an environment that includes cancer cells, upon which delivery the combination can be taken up by the cells leading to cell death.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

DETAILED DESCRIPTION

Figure 1:
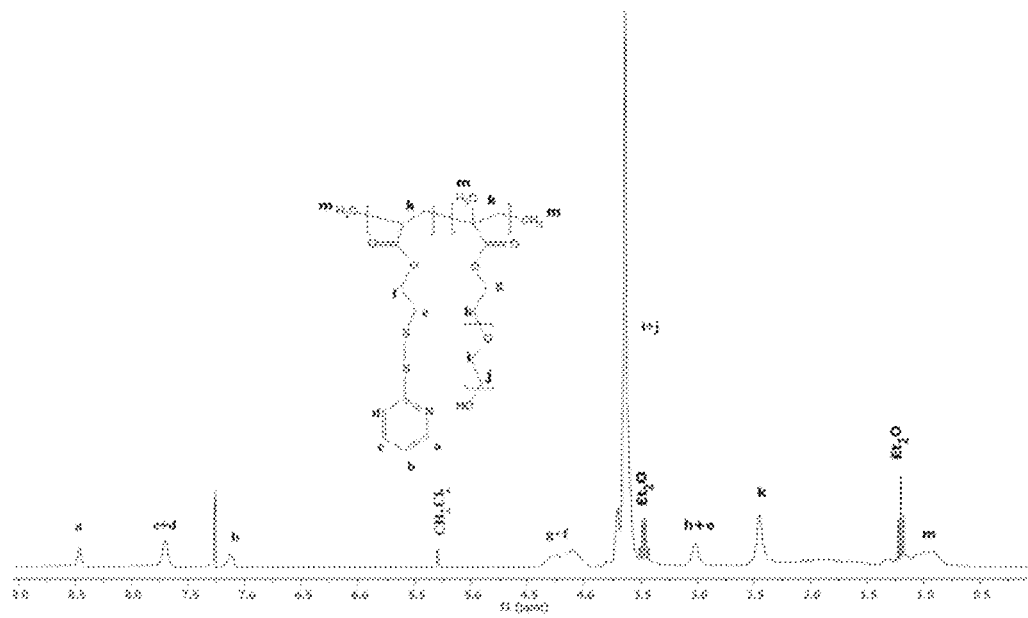
FIG. 1 is a representative $^1$H-NMR spectrum of a PDA-PEG copolymer.

Reference now will be made to the embodiments of the disclosed subject matter, one or more examples of which are set forth below. Each example is provided by way of an explanation of the subject matter, not as a limitation thereof. In fact, it will be apparent to those skilled in the art that various modifications and variations can be made without departing from the scope or spirit of the invention. For instance, features illustrated or described as one embodiment can be used on another embodiment to yield still a further embodiment. Thus, it is intended that the present disclosure cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

The term "organic" is used herein to refer to a class of chemical compounds that are comprised of carbon atoms. For example, an "organic polymer" is a polymer that includes carbon atoms in the polymer backbone, but may also include other atoms either in the polymer backbone and/or in side chains extending from the polymer backbone (e.g., oxygen, nitrogen, sulfur, etc.).

As used herein, the term "polymer" generally includes, but is not limited to, homopolymers; copolymers, such as, for example, block, graft, random and alternating copolymers; and terpolymers; and blends and modifications thereof. Furthermore, unless otherwise specifically limited, the term "polymer" shall include all possible geometrical configurations of the material. These configurations include, but are not limited to isotactic, syndiotactic, and random symmetries.

The "number average molecular weight" ($M_n$) is readily calculated by one of ordinary skill in the art, and generally refers to the ordinary arithmetic mean or average of the molecular weights of the individual macromolecules. It is determined by measuring the molecular weight of n polymer molecules, summing the weights, and dividing by n, such as represented in the formula:

$$\overline{M}_n = \frac{\sum_i N_i M_i}{\sum_i N_i}$$

in which $N_i$ is the number of molecules of molecular weight $M_i$.

The number average molecular weight of a polymer can be determined by gel permeation chromatography, viscometry (Mark-Houwink equation), and all colligative methods, like vapor pressure osmometry or end-group determination.

The "weight average molecular weight" ($M_w$) is readily calculated by one of ordinary skill in the art, and generally refers to:

$$\overline{M}_w = \frac{\sum_i N_i M_i^2}{\sum_i N_i M_i}$$

in which $N_i$ is the number of molecules of molecular weight $M_i$.

The weight average molecular weight can be determined by light scattering, small angle neutron scattering (SANS), X-ray scattering, and sedimentation velocity.

The polydispersity index (PDI) is a measure of the distribution of molecular mass in a given polymer sample. The PDI calculated is the weight average molecular weight divided by the number average molecular weight. It indicates the distribution of individual molecular masses in a batch of polymers. The PDI has a value equal to or greater than 1, but as the polymer chains approach uniform chain length, the PDI approaches unity (i.e., 1).

The present disclosure is generally directed to polymeric materials that can selectively target and kill cancer cells. More specifically, the material can include a copolymer that is the reaction product of a biocompatible hydrophilic polymer and pyridine-2-thiol containing monomer. The copolymer reaction product can include pyridine-2-thiol side groups pendant to the backbone via a disulfide linkage. The hydrophilic component can form the polymer backbone and/or can form hydrophilic pendant groups off of the backbone. In addition, the material can include copper ions in combination with the copolymer. The copper ions can be associated with the copolymer according to any relationship. For instance, the copper ions can be associated with the copolymer via formation of a complex between the pyridine functionality and the copper ions, but the association is not limited to the formation of a complex and other associations are encompassed herein.

In one embodiment, upon formation, the copolymer can self-assemble in the form of a particle, e.g., a nanoparticle, that can be suitable for safe and effective cancer therapy with the hydrophilic component of the copolymer being at the exterior surface of the particle. The formation of the nanoparticle can endow two advantages for cancer therapy. First, due to the existence of the hydrophilic corona (e.g., polyethylene glycol), the circulation time of the copolymer in the blood stream can be greatly extended. Second, by taking advantage of the leaky structure of the capillaries in the tumor tissue, the formed nanoparticle can be enriched in the tumor through the so called enhanced permeability and retention (EPR) effect.

Without wishing to be bound to any particular theory, it is believed that the polymer/$Cu^{2+}$ based nanoparticle can target and enter cancer cells through interaction with exofacial thiols. Following cellular take-up, the pyridine-2-thiol-$Cu^{2+}$ component of the side groups can be released from the polymer backbone via GSH action, leading to cell death. In addition, RNA microarray analysis as further described in the examples section indicates that the materials can decrease upregulation of oncogenes (e.g., CIRBP and STMN1) and increase downregulation of tumor suppressor genes (e.g., CDKN1C and GADD45B) in cancer cells, to further enhance desirable activity on cancer cells.

Beneficially, the polymer/$Cu^{2+}$ materials are non-toxic to non-cancer cells and as such can be utilized with little or no side effects. Due to the differences between normal and cancer cells in intracellular GSH level as well as expression level of various genes, the disclosed materials can exhibit high selectivity in killing a broad spectrum of cancer cells, including drug resistant cancer cells, while sparing normal cells. The combination of minimal side effects, enhanced efficacy, longer half-life, exclusive selectivity for cancer cells, and wide-spectrum of anticancer activity can provide a successful approach to cancer therapy. For instance, the disclosed materials can be effective in treating ovarian cancer, breast cancer, cervical cancer, prostate cancer, lung cancer and leukemia, among others.

The hydrophilic component of the polymer can be based upon any biocompatible polymer or oligomer capable of reacting with the desired pyridine-2-thiol monomers. By way of example and without limitation, the hydrophilic component can include one or more of polyethylene glycol, poly(N-isopropylacrylamide) (polyNIPAAm), poly(N-(2-hydroxypropyl)methacrylamide) (polyHPMA), poly(acrylic acid) (PAAc), poly(DL-lactic acid-co-glycolic acid) PLGA, poly(L-histidine), etc.

In one particular embodiment, the copolymer can be formed by reaction of pyridine-2-thiol monomer with poly-ethylene glycol)methacrylate having the general structure:

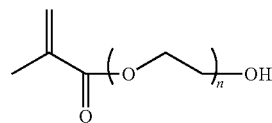

For instance, polyethylene glycol methacrylate used in a formation process can include polymers in which n in the above structure is from about 4 to about 1,000, from about 5 to about 100, or from about 6 to about 20 in some embodiments.

The hydrophilic polymer can react with one or more pyridine-2-thiol monomers to form the polymer that includes the pyridine-2-thiol pendant groups. By way of example, and without limitation, pyridine-2-thiol monomers can include one or more of:

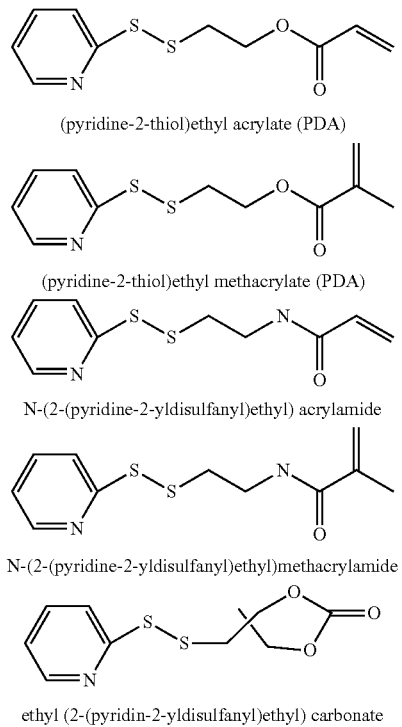

This reaction can be facilitated by any suitable catalyst. For example, the catalyst used in the reaction can be, in particular embodiments, azobisisobutyronitrile (AIBN), benzoyl peroxide, potassium persulfate, or combinations thereof. The polymerization can be free radical polymerization or living radical polymerization including stable free radical mediated polymerization (SFRP), atom transfer radical polymerization (ATRP), reversible addition-fragmentation chain transfer (RAFT) polymerization, and iodine-transfer polymerization. The last monomer of the above examples (ethyl(2-(pyridin-2-yldisulfanyl)ethyl)carbonate) can be polymerized using isopropanol as an initiator and Sn(Oct)2 as a catalyst through ring-opening polymerization.

Following the polymerization reaction, a copolymer can be formed that includes pyridine-2-thiol containing units pendant to the backbone of the polymer. For instance, in those embodiments in which the pyridine-2-thiol monomer is polymerized with a polyethylene glycol)methacrylate, the resulting copolymer can include pendant groups of the pyridine-2-thiol component, e.g., (pyridine-2-thiol)ethyl acrylate groups and pendant groups of the hydrophilic polymer, e.g., (polyethylene glycol)methacrylate groups and can have the following general structure:

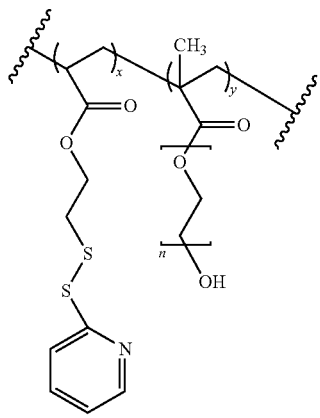

As can be seen, in this particular embodiment, the hydrophilic component of the copolymer will form pendant groups upon the polymerization reaction. In such embodiments, the molar ratio of the pyridine-2-thiol containing repeating units of the polymer to hydrophilic pendant repeating units of the polymer (e.g., the polyethylene glycol) methacrylate units) can be from about 100:1 to about 1:100 (the ratio of x to y in the above structure), for instance from about 20:1 to about 1:20 in some embodiments, from about 10:1 to about 1:10 in some embodiments, or about 1:1 in some embodiments.

It should be understood that the hydrophilic polymer that is copolymerized with the pyridine-2-thiol containing monomer need not necessarily form secondary pendant groups as is the case with the polyethylene glycol)methacrylate copolymerization process, and in some embodiments, the only pendant groups formed upon reaction of the hydrophilic polymer and the pyridine-2-thion containing monomers can be the pyridine-2-thiol containing groups. Moreover, in either case, and as discussed further below, the copolymer can optionally further contain additional pendant groups that are developed via reaction with a third monomeric component.

In addition, although shown as a block copolymer in the above structure, it is to be understood that this representation is simply short-hand for any type of copolymer (e.g., random, block, etc.) that includes repeating units of both the pyridine-2-thiol repeating units and repeating units of the hydrophilic polymer.

The pyridine-2-thiol containing copolymer can generally have a weight average molecular weight from about 1,000 to about 100,000, or from about 5,000 to about 35,000 in some embodiments. In one embodiment, the copolymer can have a PDI of from about 1.05 to about 3, or from about 1.15 to about 1.30 in some embodiments.

In one embodiment, the copolymer can be further processed to include one or more additional copper chelator functionalities. For instance, chelators can form a complex with copper by thiol, amine, and/or hydroxyl, one or more of which can be included on the copolymer in addition to the pyridine functionality of the pyridine-2-thiol via further processing of the copolymer. By way of example, in one embodiment, a copolymer as described above can be reacted with a thiol monomer that contains a carbon-bonded sulfhydryl (i.e., —C—SH or R—SH group where R represents an alkane, alkene, or other carbon-containing chain) through a thiol-disulfide exchange reaction to substitute a portion of the end groups of the pyridine-2-thiol monomer in the copolymer. For instance, a portion of the 2-(pyridin-2-yldisulfanyl)ethyl acrylate repeating units in the copolymer illustrated above can be converted to be have a modified end group. This end group can include additional copper association functionality or alternatively, can be further reacted with another monomer to bond the copper associating functionality to the copolymer.

Any suitable thiol monomer can be utilized in the thiol-disulfide exchange reaction, including but not limited to, alkythiols having a carbon chain of about 2 to about 20 (e.g., ethanethiol, propanethiol, butanethiol, pentanethiol, etc.) generally with a functional end group opposite of the thiol group (e.g., a carboxylic group, a hydroxyl end group, an amine end group, etc.). In one embodiment, the thiol monomer can have the formula:

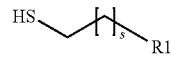

where s is 1 to 19 and R1 is H, a hydroxyl group (—OH), a carboxyl group (—COOH), an aldehyde group (—CHO), an amine group (—NH$_2$), an amide group (—CONH$_2$), an amino acid, a peptide chain of at least two amino acids (e.g., arginylglycylaspartic (RGD) acid), or another organic end group.

The reaction can take place by mixing the copolymer with thiol monomer in any suitable solvent for them such as water, methanol, ethanol, dimethyl sulfoxide, methylene chloride.

In one embodiment, the copolymer can be processed to include a polyhydroxy containing pendant group that can provide polyhydroxyl functionality to the copolymer for increased copper association capability. By way of example, following initial thiol disulfide exchange reaction to include a functional end group on copolymer pendant groups (e.g., an amine group), the functional end groups can be further reacted with a polyhydroxy carboxylic acid to provide a polyhydroxy pendant group on the copolymer.

Polyhydroxy carboxylic acids can include cyclic or aliphatic hydroxy monocarboxylic acids of about 5 or more carbon atoms and containing about 3 or more hydroxy groups bound to adjoining carbon atoms. In one embodiment, the polyhydroxy carboxylic acids can include those obtainable by the oxidation of sugars. For example, arabonic acid, gluconic acid, galactonic acid and lactobionic acid can be utilized. Polyhydroxy carboxylic acids obtainable by other methods are also encompassed such as, and without limitatino, glucoheptonic acid and mannoheptonic acid.

Through this reaction, about 1 molar % to about 50 molar % (e.g., about 5 molar % to about 25 molar %) of the pyriding-2-thiol repeating units of the initial copolymer can be converted to modify a portion of the end groups of the copolymer. As such, the resulting modified copolymer can include the modified disulfanyl repeating units in an amount that is about 1 molar % of the pyridine-2-thiol repeating units to about 50% of the pyridine-2-thiol repeating units in the modified copolymer.

By way of example, upon the initial exchange reaction, a resulting modified copolymer can include the 2-(pyridin-2-yldisulfanyl)ethyl acrylate repeating units, poly(ethylene glycol)methacrylate repeating units, and modified disulfanyl repeating units that can include a chelating agent or can be further reacted to include a chelating agent. In one embodiment, the modified disulfanyl repeating units can include functionality for further reaction with a polyhydroxy carboxylic acid, e.g., an amine. In this embodiment, upon the initial exchange reaction, the modified copolymer can have the following general structure:

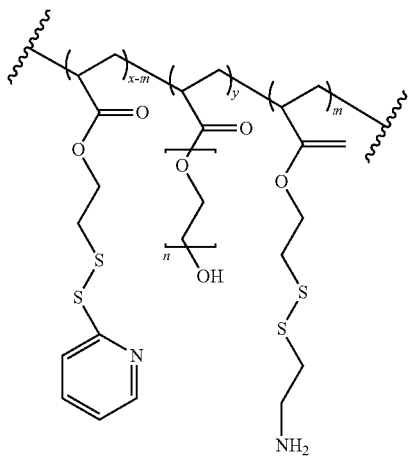

This copolymer can then be reacted with a polyhydroxy carboxylic acid, e.g., lactobionic acid, to render the copolymer having the following general structure that includes pyridine functionality in conjunction with polyhydroxy functionality:

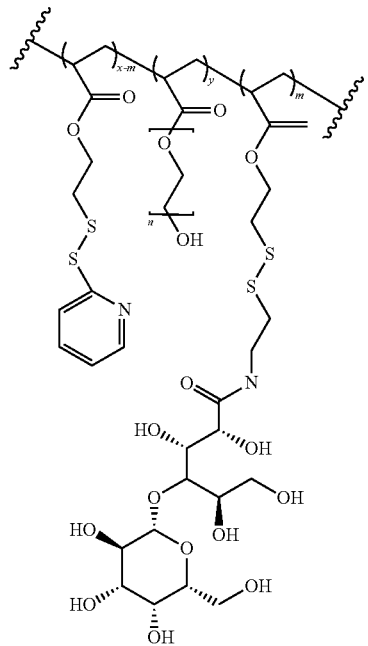

As discussed above, such a polymer can have a ratio of x to y that is from about 100:1 to about 1:100 (i.e., the molar ratio of the disulfanyl monomers (total) to the backbone forming monomer that is about 100:1 to about 1:100) and of the total disulfanyl monomers, from about 1% of x to about 50% of x (i.e., about 1 molar % to about 50 molar % (e.g., about 5 molar % to about 25 molar %) can include the secondary functionality (e.g., polyhydroxy functionality). Although shown as a block copolymer, it is to be understood that this representation is simply short hand for any type of copolymer (e.g., random, block, etc.) that includes repeating units as described.

The materials may be delivered or administered acutely or chronically according to various delivery methods, including sustained release methods, intravenous delivery, osmotic pumps, inhalation, and so forth.

Compositions for parenteral delivery, e.g., via injection, can include pharmaceutically acceptable aqueous and non-aqueous carriers, diluents, solvents or vehicles such as, without limitation, water, ethanol, polyols (e.g., glycerol, propylene glycol, polyethylene glycol and the like), carboxymethylcellulose and suitable mixtures thereof, vegetable oils (e.g., olive oil) and injectable organic esters such as ethyl oleate. In addition, the composition can contain minor amounts of auxiliary substances such as wetting or emulsifying agents, pH buffering agents and the like that can enhance the effectiveness of the biologically active compound. These compositions may also contain adjuvants such as preservatives, wetting agents, emulsifying agents and dispersing agents.

Prevention of the action of microorganisms may be ensured by the inclusion of various antibacterial and antifungal agents such as paraben, chlorobutanol, phenol, sorbic acid and the like. It may also be desirable to include isotonic agents such as sugars, sodium chloride and the like.

A composition can include one or more oil-soluble antioxidants including, without limitation, butylated hydroxytoluene (BHT), ascorbyl palmitate, butylated hydroxyanisole (BHA), α-tocopherol, phenyl-a-naphthylamine, hydroquinone, propyl gallate, nordihydroguiaretic acid, and mixtures thereof as well as any other known oil-soluble antioxidant compatible with the other components of the compositions. Mineral oils, animal oils, vegetable oils and silicones can be incorporated in a topical creams or lotions as disclosed herein. In addition to such oils, other emollients and surface active agents can be incorporated in an emulsion.

Thickeners such as natural gums and synthetic polymers, as well as preservatives such as methylparaben, butyl paraben, propylparaben and phenyoxyethanol, can be included. Other active ingredients such as sunscreen materials and antimicrobial materials may be utilized in a composition, provided, of course, that they are physically and chemically compatible with the other components of the composition.

A composition may also contain, as optional additions, one or more soluble or dispersible pharmaceutically acceptable ingredients generally used in pharmaceutical emulsion compositions. Typical such ingredients include, for example, a preservative or antioxidant such as methyl or propyl paraben, butylated hydroxyanisole, imidazolidinyl urea and the like; a water or oil soluble vitamin such as vitamin C, tocopheryl linoleate and the like; and/or a colorant, odorant, humectant, thickener and the like. In general, from about 0.1 to about 15 percent total weight of such optional additives may be incorporated into a composition, depending upon the solubility or miscibility characteristic of the particular additive, it can be incorporated into whichever emulsion phase is most suitable.

A composition may be made into a wide variety of product forms suitable for, e.g., topical administration onto the skin of a subject or internal administration to the lungs, digestive tract, or vasculature. Non-limiting examples for topical administration include a lotion, an ointment, a gel, a cream, a stick, a spray, an aerosol, foam, a paste, etc.

Each additive of a composition may generally constitute between about 0.05% to about 15% of the total weight of the formulation. In one embodiment, a composition can include an additive in an amount between about 0.05% and about 10% or between about 0.05% and about 8%, or between about 0.05% and about 7%, or between about 0.05% and about 6%, or between about 0.05% and about 5% of the total weight of the formulation.

According to one embodiment, the delivery agents can be delivered in the form of an aerosol spray, from a pressurized pack or a nebulizer, for lung applications, for instance in treatment of a cancer in which the lung is affected. Additional formulations for administration may be made in accordance with methods and amounts known in the art.

The present disclosure may be better understood with reference to the examples, set forth below.

Example 1

Aldrithiol-2 and Silica gel (Spherical, 100 mm) were purchased from Tokyo Chemical Industry Co., LTD (Harborgate Street, Portland, Oreg.). 2-Mercaptoethenol, DL-dithiothreitol (DTT), tris(2-carboxyethyl)phosphine (TCEP), 2,2-Azobisisobutyronitrile (AIBN), (3-(4,6-dimethylthiazol-2-yl)-2,5-diphenyltetrazolium bromide (MTT), Propidium Iodide (PI) and Polyethylene glycol)methacrylate (Mn=360 Da) were purchased from Sigma Aldrich Chemical Co. (St. Louis, Mo.). Buthionine sulfoximine (BSO) and Glutathione monomethylester (GSH-MME) were purchased from Cayman Chemical (Ann Arbor, Mich.). Penicillin (10,000 U/mL), streptomycin (10,000 mg/mL), 0.25% trypsin-EDTA, Dulbecco's Modified Eagle Medium (with L-glutamine) and fetal bovine serum (FBS) were obtained from American Type Culture Collection (ATCC, Manassas, Va.). Molecular probes and RNase were purchased from Life Technologies (Grand Island, N.Y.), GSH-Glo™ Glutathione Assay kit was purchased from Promega Corporation (Madison, Wis.). Cy5-NHS was purchased from Lumiprobe Corporation (Hallandale Beach, Fla.). AH the other solvents used in this research were purchased from Sigma Aldrich Chemical Co. (St. Louis, Mo.) and used without further purification unless otherwise noted.

PDA-PEG polymer was synthesized according to methods as are known in the art. Briefly, 2-(pyridin-2-yldisulfanyl)ethyl acrylate (PDA, 241.3 mg, 1 mmol) and polyethylene glycol)methacrylate (PEG$_{360}$, Mn=360 Da, 360 mg, 1 mmol) were dissolved in 10 mL degassed anisole. 2,2-Azobisisobutyronitrile (AIBN, 14 mg, 0.085 mmol) in 1 mL degassed anisole was then added, and the reaction mixture was stirred for 24 h at 65° C. The final product was precipitated (3×) in ice cold ether and dried for 48 h in vacuum. The structure of PDA-PEG was confirmed by $^1$H-NMR, and its molecular weight and polydispersity were evaluated by gel permeation chromatography (GPC).

Figure 2:
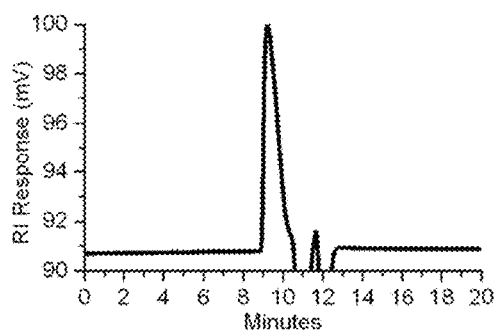
FIG. 2 is a representative GPC curve for a PDA-PEG copolymer.
Figure 3:
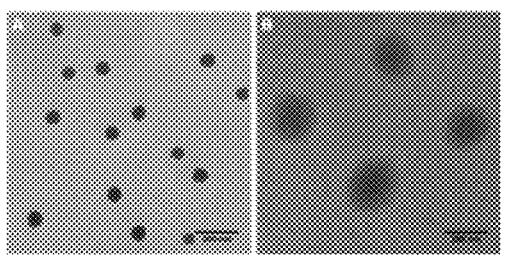
FIG. 3 presents TEM images of nanoparticles of PDA-PEG at A and PDA-PEG/Cu$^{2+}$ at B.

The successful synthesis of the polymer was verified by $^1$H-NMR (FIG. 1) and gel permeation chromatography (GPC) (FIG. 2). The $^1$H NMR result revealed that the actual ratio between PDA and mPEG in the final PDA-PEG polymer was close to their feeding ratios (1:1). GPC showed that the weight average molecular weight of PDA-PEG polymer was 41.8 kDa. Due to the co-existing of hydrophobic PDA and hydrophilic PEG, the amphiphilic PDA-PEG self-assembled into nanoparticle in aqueous solution. Zeta sizer revealed that PDA-PEG nanoparticles had a hydrodynamic size of 87.64±2.06 nm and carried negative surface charge (−15.4±2.05 mV). The morphology of PDA-PEG nanoparticle was also confirmed by TEM, which showed a spherical shape with a size around 80 nm (FIG. 3 at A).

Two methods were used to measure PDA concentration in the polymer. In the first method, PDA-PEG (50 µg/mL in DMSO) was incubated with tris(2-carboxyethyl)phosphine (TCEP, 10 mM, 20 mM and 50 mM) for 1 hour at room temperature, and then the amount of pyridine-2-thione released was quantified through UV-Vis spectrophotometer at $\lambda$=375 nm and correlated to PDA amount ($\epsilon$, molar absorption coefficient=8080 M$^{-1}$ cm$^{-1}$). In the second method, a calibration curve of pyridine-2-thione was firstly established and then applied to calculate the PDA concentration in the polymer. In brief, 100 µg aldrithiol-2 was dissolved in 1 mL DMSO and completely converted to pyridine-2-thione by adding excess TCEP (13.1 mg, 100× excess). The reaction mixture was then diluted in DMSO to obtain a serial of concentrations of pyridine-2-thione with UV-Vis absorbance between 0.1 and 1 at 375 nm. Based on the UV-Vis absorbance, the calibration curve was established. PDA-PEG (50 µg/mL in DMSO) was incubated with 10, 20 and 50 mM TCEP for 1 h. After that, PDA concentration in the polymer was calculated according to the calibration curve after measuring the UV-Vis absorbance of the polymer solution.

Figure 4:
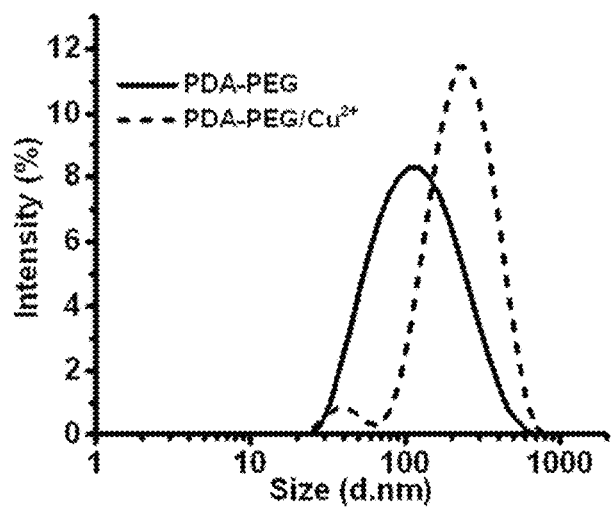
FIG. 4 presents the size distribution of nanoparticles formed from PDA-PEG polymer and PDA-PEG/Cu$^{2+}$ acquired by dynamic light scattering.

After the addition of Cu$^{2+}$ (CuCl$_2$, 10 µM) to the PDA-PEG copolymer, the hydrodynamic size of the nanoparticles increased to 196.4±0.07 nm (FIG. 4), while becoming less negatively charged (−5.47±0.86 mV). Due to the interaction between Cu$^{2+}$ and pyridine ring made the PDA segment more hydrophilic so that the core became less condensed (FIG. 3 at B), which led to the increase of the particle size.

To validate whether the polymer form of the chelator possesses similar cell killing capacity as other small molecular materials, cell proliferation assay was employed in 7 cancer cell lines (MDA-MB-231, SKOV-3, NCI/ADR-Res, UMSCC 22A, HCT 116 and HL 60), 5 normal cell lines (CONA, NIH 3T3, MCF 10A, KC and BNL CL2), and a NIH 3T3 cell line, an immortalized cell line derived from normal cells.

PDA-PEG was modified by Cy5 for cellular uptake study. Briefly, cysteamine (0.11 mg, 5% PDA function group) in 500 µL. DMSO was added dropwise into 20 mg PDA-PEG in 500 µL DSMO and the reaction mixture was kept at room temperature overnight. After overnight reaction, Cy5-NHS ester (0.39 mg in 390 µL DMSO) was added and the mixture was kept for reacting overnight, following a thoroughly dialysis towards DMSO to remove free Cy5. The concentration of Cy5 in the final product was measured by a microplate reader (SpectraMax® M5, Molecular Devices Inc) at $\lambda_{ex}$640 and $\lambda_{em}$680.

Cells were seeded in 96-well plate (20,000 cells/well) for 24 h prior to the study. Then a serial of concentrations of PDA-PEG in culture medium was added, supplementing with or without CuCl$_2$ (10 µM). The cells were then incubated 48 h in 95/5% air/CO$_2$ at 37° C. After 48 h, MTT reagent (100 µL, 10% (w/w) in medium) was added and incubated for 4 h, following the addition of MTT stop solution and the measurement of the optical density of the medium using a microplate reader (ELX808, Bio-Tech Instrument, Inc) at A=595 nm.

Figure 5:
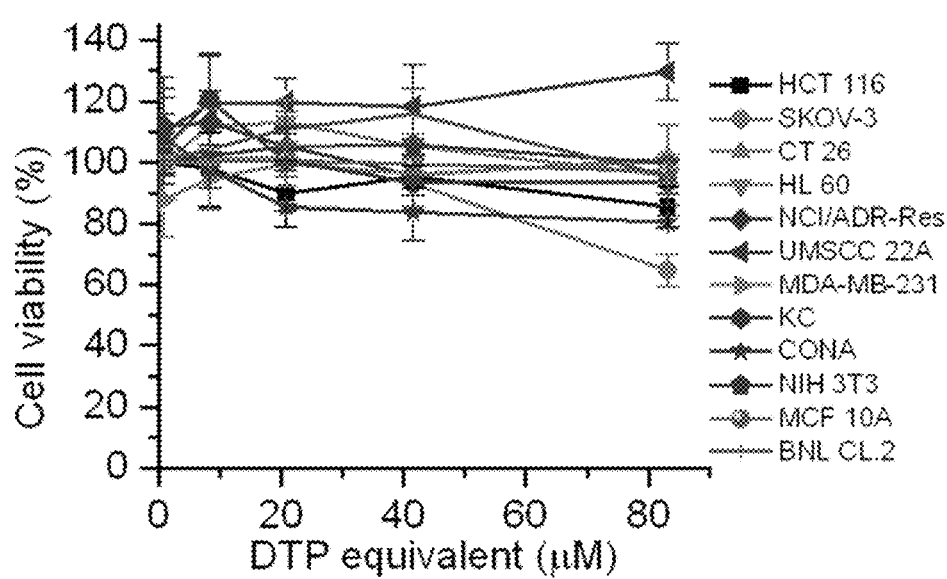
FIG. 5 presents cytotoxicity of PDA-PEG nanoparticle for different cell lines without the addition of 10 μM CuCl$_2$. Data represent the means±SD, n=3.
Figure 6:
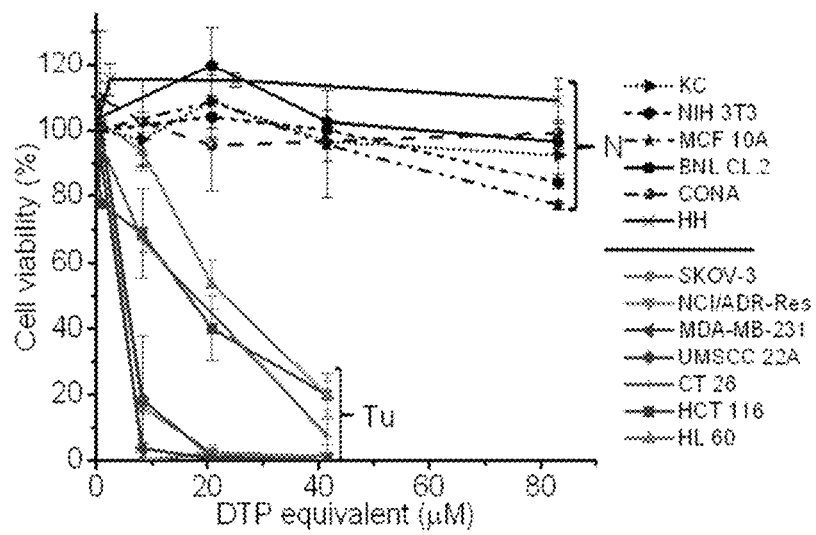
FIG. 6 presents cytotoxicity of PDA-PEG/Cu$^{2+}$ combination for normal (N) and cancer (Tu) cells. Normal cells include KC (human keratinocyte), NIH 3T3 (murine fibroblast), MCF 10A (human breast epithelial cell), BNL CL.2 (murine liver cell), CONA (CCD 841 CoN, human colon cell), and HH (human hepatocyte). Data represent the means±SD, n=3.

As expected, PDA-PEG nanoparticle did not show obvious toxicity up to the equivalent DTP concentration of 40 µM for all tested cells (FIG. 5). Similar to DTP, the addition of Cu$^{2+}$ dramatically enhanced the potency of PDA-PEG nanoparticles for cancer cells (FIG. 6). The IC$_{50}$ of PDA-PEG/Cu$^{2+}$ for SKOV-3, NCI/ADR-Res, MDA-MB-231, and UMSCC 22A cells were less than 6 μM as shown in Table 1, below, and with a IC$_{95}$ less than 20 μM.

TABLE 1

| Cell lines | IC$_{50}$ (μM) |
| --- | --- |
| MDA-MB-231 | 2.32 ± 0.33 |
| SKOV-3 | 3.83 ± 0.58 |
| NCI/ADR-RES | 4.72 ± 0.45 |
| UMSCC 22A | 5.34 ± 0.51 |
| CT 26 | 10.56 ± 0.90 |
| HCT 116 | 11.45 ± 5.35 |
| HL60 | 22.90 ± 0.83 |
| HH | >831.5 |
| BNL CL.2 | 552.02 ± 72.50 |
| CONA | 289.91 ± 70.00 |
| KC | 202.47 ± 26.56 |
| NIH3T3 | 158.70 ± 17.13 |
| MCF 10A | 135.37 ± 10.80 |

Figure 7:
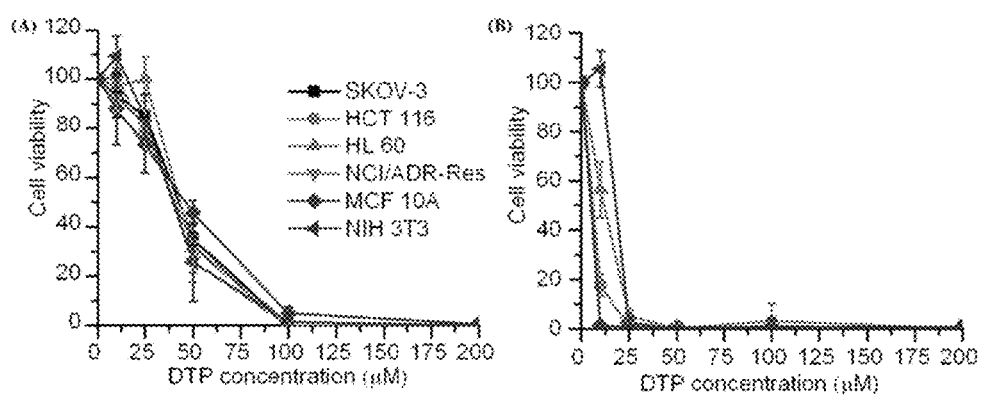
FIG. 7 illustrates the cytotoxicity of DTP for different cell lines at the absence (A) and presence (B) of 10 μM CuCl$_2$. Data represent the means±SD, n=3.
Figure 8:
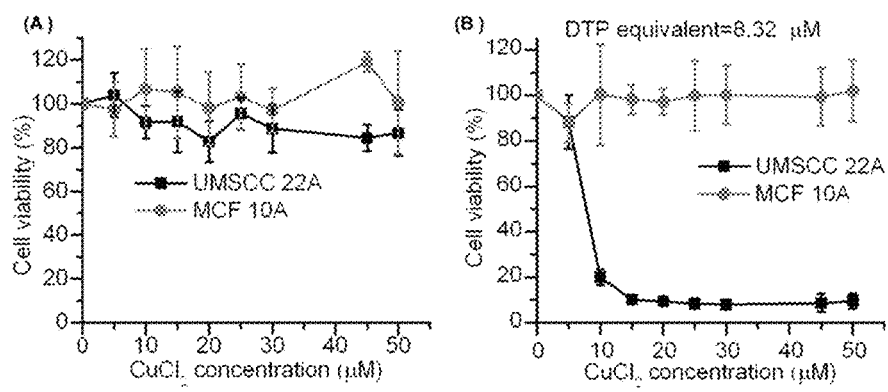
FIG. 8 presents the concentration effect of CuCl$_2$ on the cytotoxicity of medium (A) and PDA-PEG (B). PDA-PEG (8.32 μM, equivalent to DTP) was mixed with different concentrations of CuCl$_2$ and incubated with UMSCC 22A and MCF 10A for 48 h. Data represent the means±SD, n=3.

Contrary to its small molecule counterpart (FIG. 7), the cell killing effect of PDA-PEG/Cu$^{2+}$ for cancer cells and normal cells are significantly different. FIG. 6 also showed that PDA-PEG/Cu$^{2+}$ combination is non-toxicity to normal cells, including keratinocytes, fibroblasts, breast epithelial cells, colon cells, and hepatocytes, up to 80 μM. The IC$_{50}$s for normal cells were 10-70 fold higher than those for cancer cells (Table 1). All these suggested that PDA-PEG/Cu$^{2+}$ can selectively kill cancer cells, including drug resistant cancer cells, while sparing normal ones. In addition, FIG. 8 reveals that the cytotoxicity of PDA-PEG/Cu$^{2+}$ for cancer cells increased with the increase of Cu$^{2+}$ concentration, while not showing influence on normal cells.

To further validate that the PDA-PEG/Cu$^{2+}$ combination can specifically kill cancer cells versus normal ones, NIH 3T3, SKOV-3, NCI/ADR-Res, and UMSCC 22A cells were stained with different color fluorescent dyes, NIH 3T3 cell was selected as a representative normal cell because its comparable growth rate and suitability for co-culture with cancer cells in DMEM medium. All cells except NIH 3T3 were rounded up after being treated with 8.3 μM of PDA-PEG/Cu$^{2+}$, indicating these cells were not in healthy status. On the contrary, NIH 3T3 cells still kept the original stretched cell shape at 20.79 μM. Images visually confirmed the MTT results in FIG. 6. This phenomenon was also observed in the multiple cell lines co-culture model, where only NIH 3T3 cells kept their original spindle morphology, indicating that the PDA-PEG/Cu$^{2+}$ combination could selectively kill cancer cells while sparing normal cells in a more disease relevant co-culture model.

Figure 9:
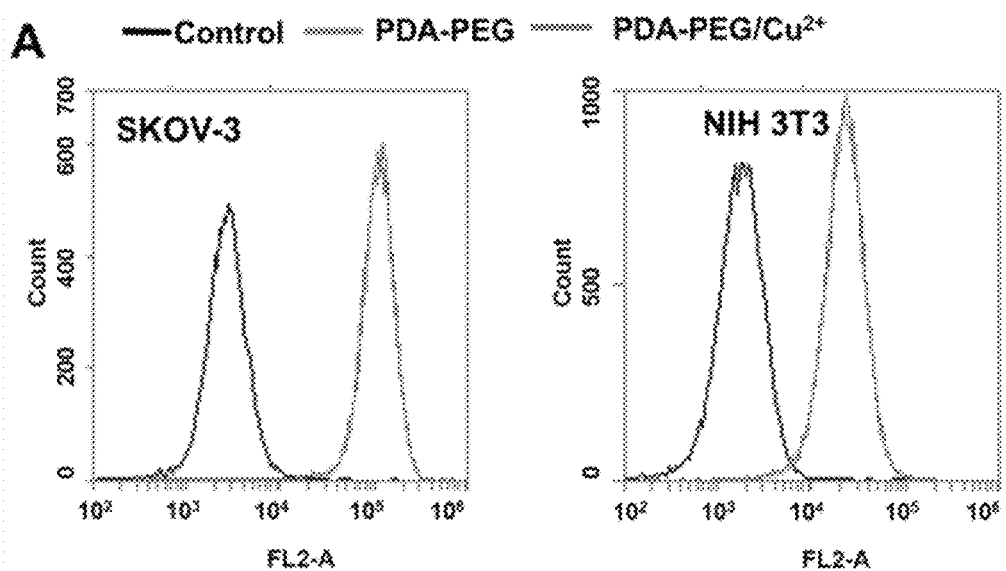
FIG. 9 presents flow cytometry spectra of SKOV-3 (left) and NIH 3T3 (right) cells. Cellular uptake assays were carried out 1 h after the addition of nanoparticles. Scale bars were 20 μm.
Figure 10:
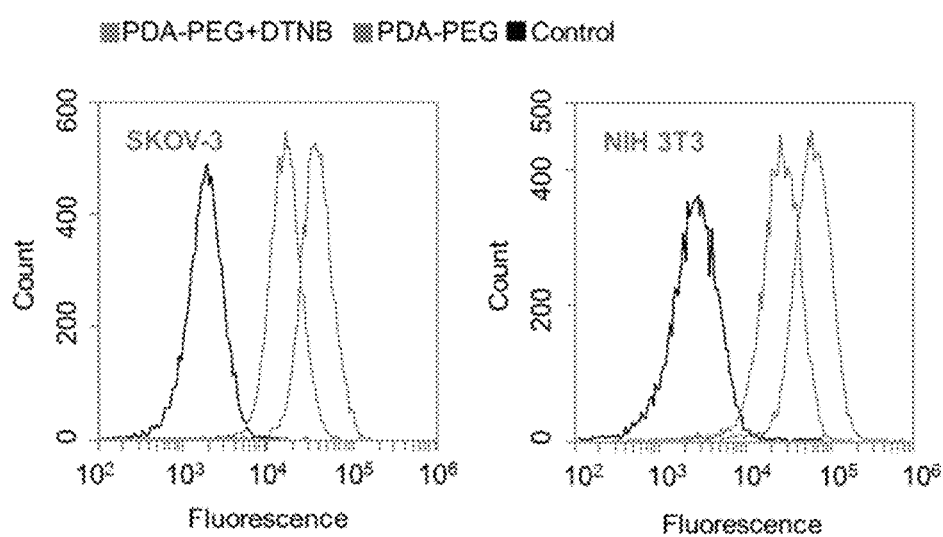
FIG. 10 presents the flow cytometry spectra of SKOV-3 (left) and NIH 3T3 (right) cells treated with Cy5 labeled PDA-PEG nanoparticles. Cellular uptake assays were carried out 1 h after the addition of nanoparticles.

To probe the mechanism for PDA-PEG/Cu$^{2+}$ selectively killing cancer cells, the cellular uptake of PDA-PEG and PDA-PEG/Cu$^{2+}$ nanoparticle was investigated with flow cytometry and confocal microscopy. As shown in FIG. 9, the nanoparticles fabricated from Cy5 labeled PDA-PEG and PDA-PEG/Cu$^{2+}$ combination entered cells with identical manners, suggesting that the addition of copper ions did not affect its entering cells. In addition, these nanoparticles showed similar efficiency in entering normal cells (NIH 3T3) and cancer cells (SKOV-3). Therefore, the uptake of PDA-PEG/Cu$^{2+}$ wasn't the reason for its cancer-cell-selectivity, 5,5'-Dithio-bis-(2-nitrobenzoic acid) (DTNB) is a compound binds the free thiol groups on the surface of cell membrane. The addition of DTNB significantly inhibited the cellular uptake of PDA-PEG, suggesting that PDA-PEG entering cells via exofacial thiol mediated endocytosis. This is believed to be due to the high density of thiol-reactive FDA segment of the PDA-PEG polymer, which can react with exofacial thiols through thiol-disulfide exchange reaction to facilitate cellular uptake. Similar blocking effect was also observed in NIH 3T3 cells treated with DTNB (FIG. 10).

As pyridine-Cu$^{2+}$ complex analogues have been reported highly toxic and extensively studied as anticancer drugs, the release of pyridine-Cu$^{2+}$ association is believed to induce cell death. The high cytotoxicity of DTP/copper combination also suggested that pyridine-2-thiol/copper combination could be the active segment for its cytotoxicity. To study the release kinetics of the PDA-PEG/Cu$^{2+}$ nanoparticles, samples were dispersed in phosphate buffers supplemented with different levels of GSH as well as serum containing media to mimic the plasma and intracellular environment. In brief, cells were seeded in 96-well plate (20,000 cells/well) for 24 h prior to the study. To investigate the PDA-PEG cytotoxicity responding to reduced intracellular GSH, cells was treated with BSO (1 mM) for 24 h and then varied concentrations of PDA-PEG with or without 10 μM CuCl$_2$ were added and incubated for another 48 h. To investigate the PDA-PEG cytotoxicity responding to increased intracellular GSH, cells were treated at the same time with GSH-MME (5 mM) and varied concentration of PDA-PEG with or without 10 μM CuCl$_2$ for 48 h. For both experiments, the cell viability was finally quantified by MTT assay.

Figure 11:
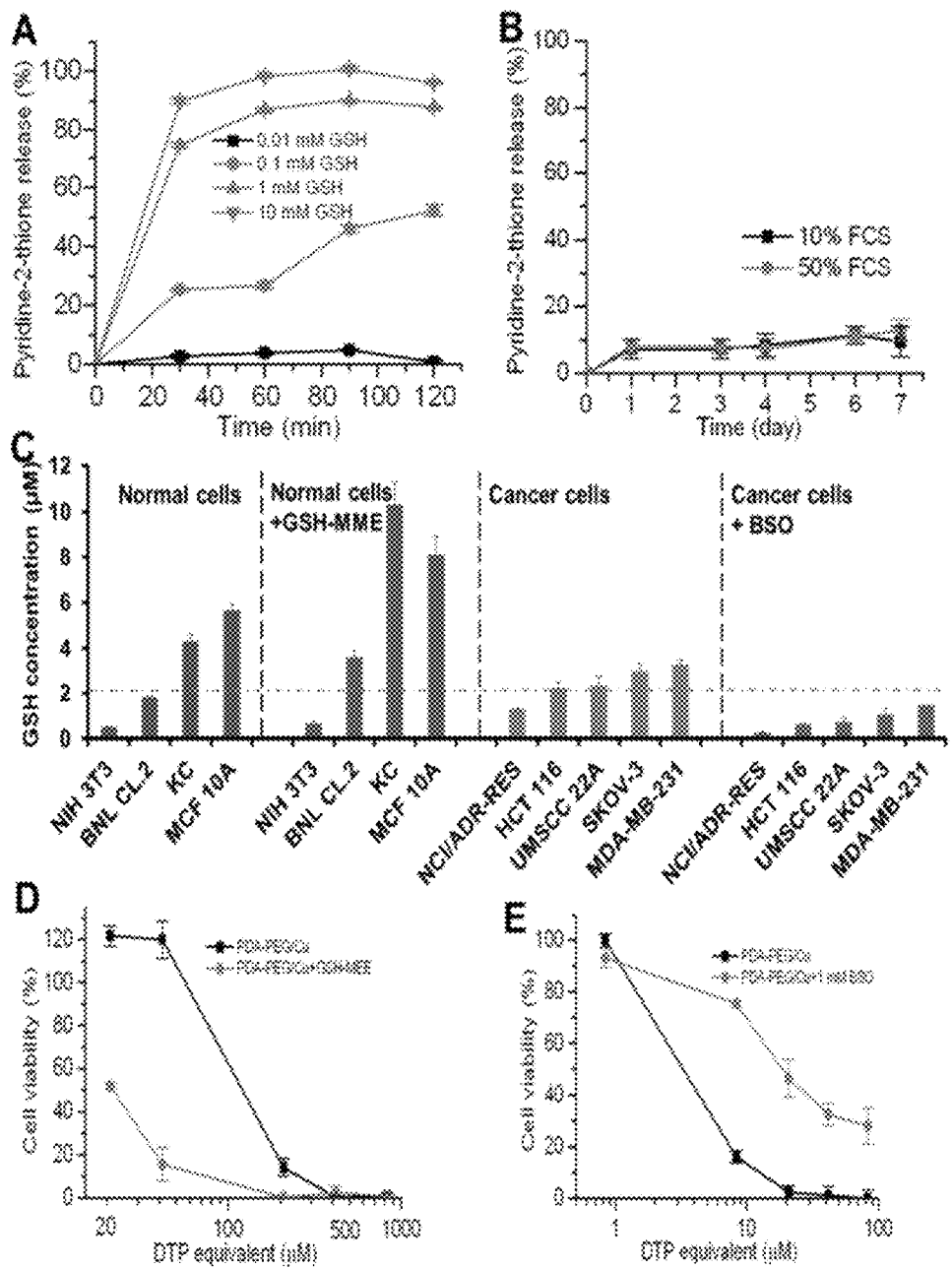
FIG. 11 presents the release kinetic of pyridine-2-thiol liberating from PDA-PEG at different GSH levels (A) and in serum containing media (B), the GSH level in different cell lines and response to the addition of GSH-MME and BSO (C), GSH-MME effect on the cytotoxicity of PDA-PEG/Cu$^{2+}$ for MCF10A cells (D), and BSO effect on the cytotoxicity of PDA-PEG/Cu$^{2+}$ combination for NCI/ADR-Res cells (E). Data represent the means±SD, n=3.

FIG. 11 at A shows that PDA-PEG/Cu$^{2+}$ was extremely stable at a low reducing environment ([GSH]<0.1 mM), such as the plasma, where has a GSH level less than 5 μM. However, almost all pyridine-2-thiol segments could be instantly released from PDA-PEG at the GSH level of 10 mM, indicating its super responsiveness to the intracellular reducing condition. Furthermore, the polymer/copper combination was very stable in 50% serum containing medium, only 12.92% pyridine-2-thiol was released after 7 days of incubation (FIG. 11 at B), suggesting its great stability during blood circulation.

Since there was no significant difference between normal cells and cancer cells in uptaking PDA-PEG/Cu$^{2+}$ nanoparticle, it is believed that the observed cancer-cell-selective-killing effect was due to the intrinsic difference between normal and cancer cells. It has been reported that GSH levels in tumor tissues, such as ovarian, head and neck, breast, and lung cancer are higher than that in normal tissues. To probe whether the high GSH level is also prevail in cancer cells in vitro, GSH-Glo™ Glutathione Assay was employed. Briefly, tumor and normal cells were seeded in 96 well white plate (5,000 cells/well) overnight prior to the study. BSO (1 mM) or GSH-MME (5 mM) in culture medium was added. For control group, only fresh culture medium was added. Cells were incubated for 8 h, and the intracellular GSH concentration was measured by GSH-Glo™ Glutathione Assay according to the manufacturer's instruction.

Figure 12:
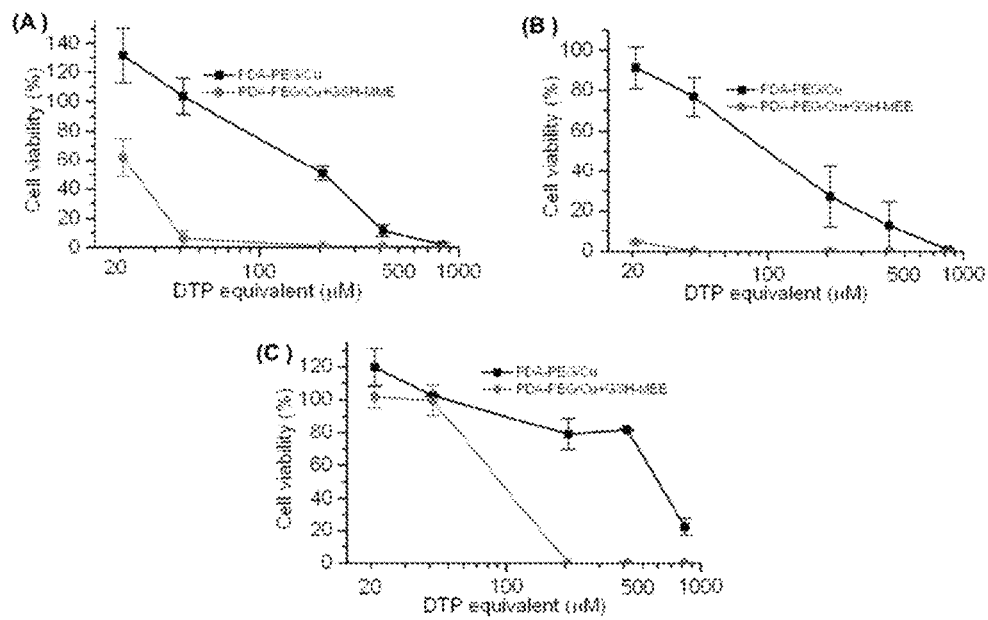
FIG. 12 illustrates the effect of GSH-MME on the cytotoxicity of PDA-PEG/Cu$^{2+}$ for KC (A), NIH 3T3 (B), and BNL.CL.2 (C) cells. Data represent the means±SD, n=3.
Figure 13:
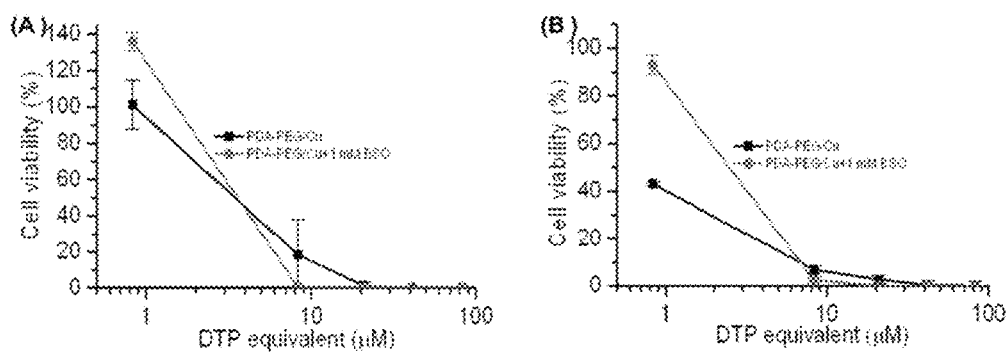
FIG. 13 illustrates the effect of BSO on the cytotoxicity of PDA-PEG/Cu$^{2+}$ for UMSCC 22A (A) and SKOV-3 cells. Data represent the means±SD, n=3.

As illustrated in FIG. 11 at C, the GSH level range in normal cells is relatively broad, ranging from 0.48 to 5.65 μM, while most tested cancer cell lines displayed relatively high GSH level (>2 μM), suggesting that intracellular GSH level could be a valid target for cancer targeted therapy. Accordingly, glutathione-monomethylester (GSH-MME, 5 mM) and buthionine sulfoxamine (BSO, 1 mM) were employed to boost or deplete the intracellular GSH level in normal cells (NIH 3T3, BNL CL.2, KC, and MCF 10A) or cancer cells (NCI/ADR-Res, HCT 116, UMSCC 22A, SKOV-3, and MDA-MB-231), respectively. After the addition of GSH-MME all normal cells exhibited higher intracellular GSH level (FIG. 11 at C). As expected, these cells became more vulnerable to the polymer/copper combination treatment (FIG. 11 at D and FIG. 12). On the contrary, BSO treated NCI/ADR-Res, UMSCC 22A, and SKOV-3 cells displayed declined GSH level. Interestingly, only NCI/ADR-Res cells became more tolerant to the polymer/copper combination treatment (FIG. 11 at E), while the other two cancer cell lines kept their sensitivity to the treatment (FIG. 13). Based on these results shown in FIG. 11, it appears that intracellular GSH level is not the sole cause for the cancer-cell-selective-killing effect of PDA-PEG/Cu$^{2+}$ nanoparticles.

Among the tested cells, there were several exceptions to this finding. First, MCF 10A and KC exhibited higher GSH level than other normal cells and cancer cell, while not sensitive to PDA-PEG/Cu$^{2+}$ treatment. Second, NCI/ADR-Res cells showed lower GSH level than other cancer cells, but still vulnerable to the treatment. Third, SKOV-3 and UMSCC 22A cells displayed lower GSH level after BSO treatment, however, the decreased GSH level only slightly abolished their response to PDA-PEG/Cu$^{2+}$ (FIG. 13). To solve these puzzles, we further investigated the gene response to PDA-PEG/Cu$^{2+}$ treatment in MCF 10A, NCI/ADR-Res, and SKOV-3 cells through RNA microarray analysis.

Briefly, cells were treated with PDA-PEG/Cu$^{2+}$ for 12 h before the RNA extraction. SKOV-3, NCI/ADR-Res, and MCF 10A (5,000,000 cells/well) were seeded in 100 mm Petri dishes (four dishes for each cell line) overnight under a humidified atmosphere of 95/5% air/CO$_2$. Culture medium was then replaced with fresh one with or without PDA-PEG (41.58 µM DTP) at the presence of 10 µM CuCl$_2$. After that, cells were incubated for another 12 h. Total RNA for gene expression analysis was isolated from cell line samples using miRNeasy Mini Kit (QIAGEN, Cat#. 217004) according to the manufacturer's instructions. Briefly, cells were scraped with 700 µL of QIAzol reagent, collected in eppendorf tube, lysed by vortexing and homogenized by centrifugation through QIAshredder columns QIAGEN, Cat#. 79656). After addition of 140 µL of chloroform, the homogenate was vigorously shaken for 15 s and centrifuged at 12,000 g for 15 min at 4° C. The RNA-containing aqueous phase was transferred to a new tube and RNA was precipitated with 525 µL of 100% ethanol. Subsequently, the sample was transfer to a RNeasy Mini spin column and centrifuged at 12,000 g for 15 s at room temperature. In the next step, RNA samples were on-column DNase treated and posteriorly washed with RPE buffer. Then, RNA was eluted from the column with 30 µL of RNase free water and quantified using a spectrophotometer. RNA quantity was assessed using an Agilent 2100 Bioanalyzer and RNA Integrity Numbers (RIN) ranged from 9.2 to 10.0.

Microarray experiments were performed using Agilent's platform. Total RNA samples were amplified and labeled using Agilent's Low Input Quick Amp Labeling Kit (Cat. #5190-2306) according to the manufacturer recommendations. Briefly, mRNA contained in 200 ng of total RNA was converted into cDNA using a poly-dT primer that also contains the T7 RNA polymerase promoter sequence. Subsequently, T7 RNA polymerase was added to cDNA samples to amplify original mRNA molecules and to simultaneously incorporate cyanine 3- or cyanine 5-labeled CTP (cRNA) into the amplification product. In addition, Agilent RNA spike-in controls (Cat#5188-5279) were added to samples prior cDNA synthesis and were used as experimental quality control. In the next step, labeled RNA molecules were purified using Qiagen's RNeasy Mini Kit (Cat.#74104). After spectrophotometric assessment of dye incorporation and cRNA yield, samples were store at −80° C. until hybridization. Labeled cRNA samples were hybridized to SurePrint G3 Human Gene Expression 8×60K v2 Microarrays (Cat.# G4858A-039494) at 65° C. for 17 h using Agilent's Gene Expression Hybridization Kit (Cat.#5188-5242) according to the manufacturer's recommendations. Two (2) control sample replicates we hybridized against two (2) polymer treated sample replicates in a dye swap design. After washes, arrays were scanned using an Agilent DNA Microarray Scanner System (Cat.# G2565CA).

Microarray analysis data revealed that for untreated cells, the RNA levels of oncogenes (CIRBP and STMN1) were upregulated, while tumor suppressor genes (CDKN1C and GADD45B) were downregulated in both ovarian cancer cell lines. Surprisingly, PDA-PEG/Cu$^{2+}$ treatment reversed the above gene expression pattern by downregulating the RNA level of CIRBP and STMN1 (>3 folds), while upregulating CDKN1C and GADD45B (>5 folds) as shown in Table 2, below.

TABLE 2

|  | SKOV-3 | NCI/ADR-Res | MCF10A |
| --- | --- | --- | --- |
| Ocogene | | Fold of Change | |
| CIRBP | 4.25↓ | 9.04↓ | 1.11↓ |
| STMN1 | 4.74↓ | 3.10↓ | 1.22↓ |
| Tumor suppressor gene | | | |
| CDKN1C(p57) | 20.55↑ | 10.72↑ | 1.06↑ |
| GADD45B | 16↑ | 5.45↑ | 1.01↑ |

Interestingly, no obvious expression level change of these genes was detected in the normal breast cell line. Other studies have shown that oncogenes (CIRBP and STMN1) are upregulated while tumor suppressor genes (CDKN1C and GADD45B) are downregulated in various types of cancers. Since the upregulated oncogenes and downregulated tumor suppressor genes stimulate cancer cell proliferation and promote tumor growth, reversing those malregulated genes through PDA-PEG/Cu$^{2+}$ treatment can result in cancer cells apoptosis.

For MCF 10A cells, although the high level of GSH can release a large amount of pyridine-2-thiol intracellularly, cells still survived due to that those oncogenes and tumor suppressor genes are not sensitive to the treatment. For NCI/ADR-Res cells, whose GSH level is relatively low but still high enough to release needed pyridine-2-thiol to regulate their oncogenes and tumor suppressor genes due to its high sensitivity. Similarly, BSO decreased the GSH level in SKOV-3 and UMSCC 22A cells, while the resulted GSH level is still high enough to release pyridine-2-thiol to regulate their oncogenes and tumor suppressor genes. Therefore, the cancer-cell-selective-killing property of PDA-PEG/Cu$^{2+}$ is believed to include the combination effects of high intracellular GSH level and the malregulation of oncogenes and tumor suppressor genes in cancer cells.

Figure 14:
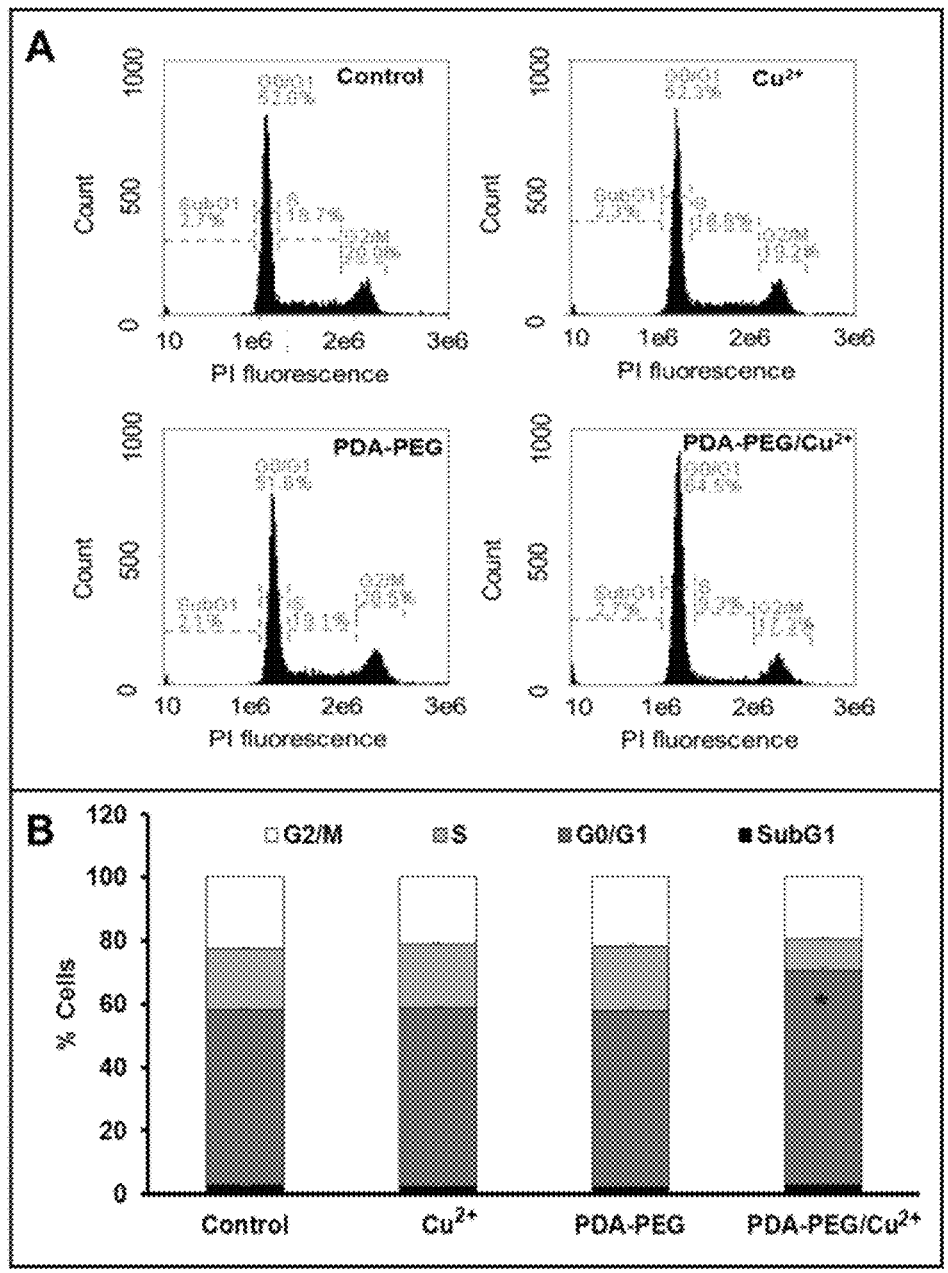
FIG. 14 presents cell cycle analysis of SKOV-3 cells after treated with 41.58 µM of PDA-PEG/Cu$^{2+}$ for 12 h. Flow cytometry spectra (A) and quantitive analysis (B) of cell cycle. Data represent the means±SD, n=3. *p<0.01.

CDKN1C is an inhibitor for G1 cyclin/Cdk complexes and causes cell arrest in G1 phase. To investigate the effect of CDKN1C up-regulation after PDA-PEG/Cu$^{2+}$ treatment, cell cycle analysis was employed. FIG. 14 illustrates that PDA-PEG/Cu$^{2+}$ inhibited cell division and arrested cancer cells in G1 phase, which could induce cell apoptosis. As expected, PDA-PEG polymer or Cu$^{2+}$ on alone did not show any effect on the cell cycle distribution of SKOV-3 cells.

Example 2

2,2'-Dithiodipyridine (TCI America, Japan, 22.70 mmol, 5.0 g) was dissolved in 25 mL methanol, following the addition of 333 μL Acetic Acid. 2-Mercaptoethanol (Aldrich, USA, 22.81 mmol, 1.7825 g, 1.6 mL) was also added dropwise into the solution. After adding 2-Mercaptoethanol, the solution became yellow. The reaction was left for 24 h at room temperature, darkness and under $N_2$ protection. The solvent was then removed under reduced pressure and the crude product (yellow oil) was purified by gravity column chromatography using silica gel (size 100 μm) as stationary phase and the mixture of ethyl acetate and hexane (15/85, v/v) as mobile phase. The product was collected, following the evaporation of eluent under reduced pressure and dryness for 48 hours in vacuum. The structure of PDA-OH was confirmed by $^1$H-NMR.

PDA-OH (1.6 g, 8.54 mmol) was dissolved in 20 mL anhydrous dichloromethane, followed by the addition of triethanolamine (TEA, 3.58 mL, 32.26 mmol). The mixture was cooled in ice for 30 min. Acryloyl chloride (1.3 mL, 16.1 mmol) in 10 mL cold anhydrous dichloromethane was then added dropwise to the PDA-OH solution and left for overnight at room temperature and darkness. The TEA salt was removed by precipitating (3×) with ice cold ether and followed by gravity column chromatography using silica gel (size 100 μm) as stationary phase and ethyl acetate/hexane (15/85, v/v) as mobile phase. The product was collected, following the evaporation of eluent and dryness for 48 h in vacuum. The structure of PDA-OH was confirmed by $^1$H-NMR.

Figure 15:
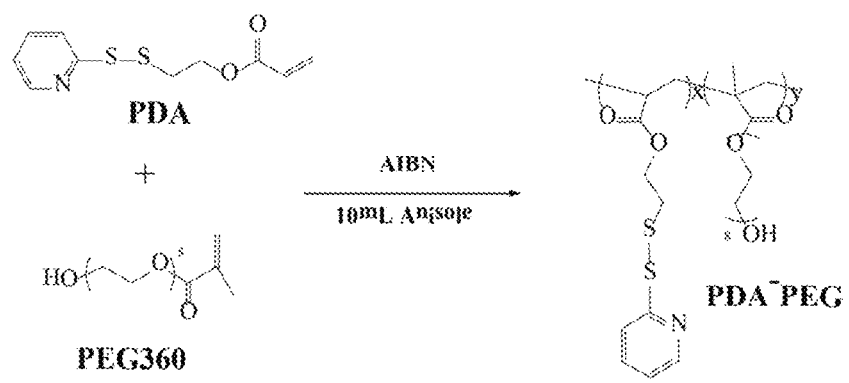
FIG. 15 presents a reaction scheme for formation of a pyridine-2-thiol copolymer.

PDA-PEG polymer was synthesized by free radical polymerization. Typically, PDA (241.3 mg (1 mmol), 482.6 mg (2 mmol) or 965.2 mg (4 mmol),) and PEG360 (360 g, 1 mmol) were dissolved in 10 mL degassed anisole. 2,2-azobisisobutyronitrile (AIBN, 14 mg (0.085 mmol), 21 mg (0.126 mmol) or 35 mg (0.213 mmol)) in 1 mL degassed anisole was then added, and the reaction mixture was stirred for 24 hours at 65° C. The final product was precipitated (3×) in ice cold ether and dried for 48 h in vacuum. The reaction scheme is illustrated in FIG. 15.

The structure of PDA-PEG was confirmed by $^1$H-NMR, and its molecular weight and polydispersity were evaluated by gel permeation chromatography (GPC).

For the quantification of side chain functionality, PDA-PEG (1.0 rang/mL in DMSO) was incubated with dithiothreitol (DTT, 10 mM) for 1 hour at room temperature, and then the amount of 2-pyridinethione released was quantified through UV-Vis spectrophotometer at λ=375 nm (ϵ, molar absorption coefficient=8080 $M^{-1}$ $cm^{-1}$)

Figure 16:
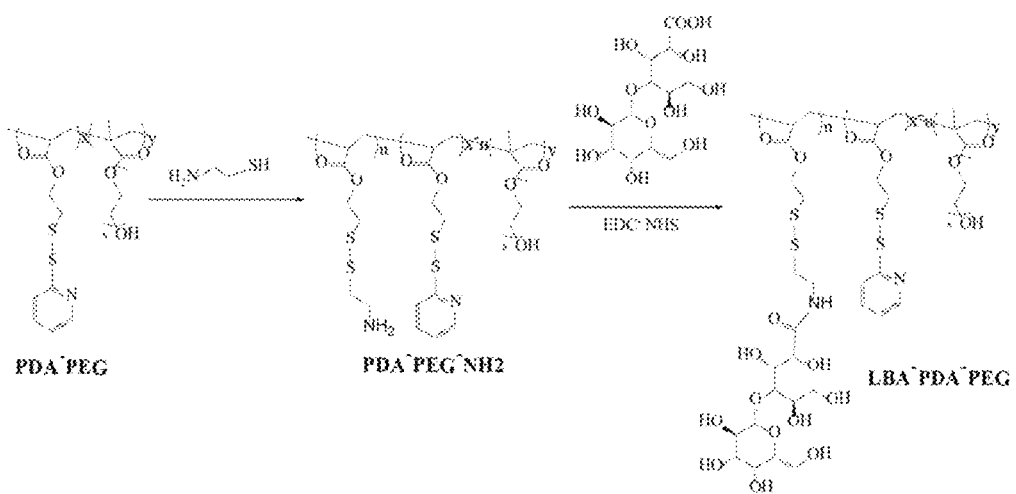
FIG. 16 presents a reaction scheme for formation of another pyridine-2-thiol copolymer.

To form a copolymer including polyhydroxy functionality, PDA-PEG (20 mg in 500 μL DMSO) was added with cysteamine (0.439 mg in 500 μL DMSO), and the mixture was stirred overnight at room temperature. Following lactobionic acid (1.73 mg in 100 μL DMSO), 1-Ethyl-3-(3-dimethylaminopropyl)carbodiimide (EDC, 1.85 mg in 50 μL DMSO) and N-Hydroxysuccinimide (NHS, 1.11 mg in 50 μL DMSO) were added and reacted for 12 h. The copolymer was formed according to the reaction scheme illustrated in FIG. 16.

To form copper combinations with the copolymers, LBA-PDA-PEG and PDA-PEG (10 mg in 500 μL DMSO) were added with $CuCl_2$ (6.5 mg in 500 μL $CH_3OH$), respectively and reacted for 12 h at room temperature. Then the reaction mixture was dialyzed towards DI water (MWCO=1,000 Da) to remove free $CuCl_2$. The PDA concentration in the combinations were quantified by UV-Vis spectrophotometer at λ=375 nm (ϵ, molar absorption coefficient=8080 $M^{-1}cm^{-1}$)

In vitro cytotoxicity of PDA-PEG and PDA-PEC-Cu combination was tested in MCF-7, SKOV-3, HepG2, HCT116, NCI/ADR-RES, CT-26, UMSCC22A, NIH3T3, and MCF-10A cell lines. Cells were seeded hi 96-well plate (20,000 cells/well) for 24 h prior to the study. Then a serial of concentrations of PDA-PEG, PDA-PEG-Cu in culture medium was added, supplementing with or without copper chloride (10-30 μM). The cells were then incubated 48 h in 95/5% air/$CO_2$ at 37° C. After 48 h, MTT reagent (100 μL, 10% (w/w) in medium) was added and incubated for 4 h, following the addition of MTT stop solution and the measurement of the optical density of the medium using a microplate reader (ELX808, Bio-Tech Instrument, Inc) at λ=595 nm.

Figure 17:
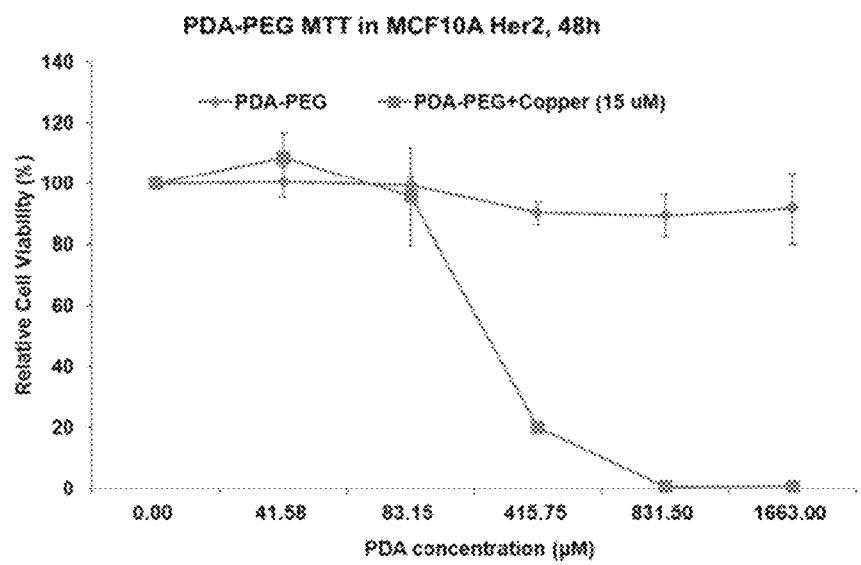
FIG. 17 demonstrates the cytotoxicity of disclosed material with MCF10A-Her2 cells.
Figure 18:
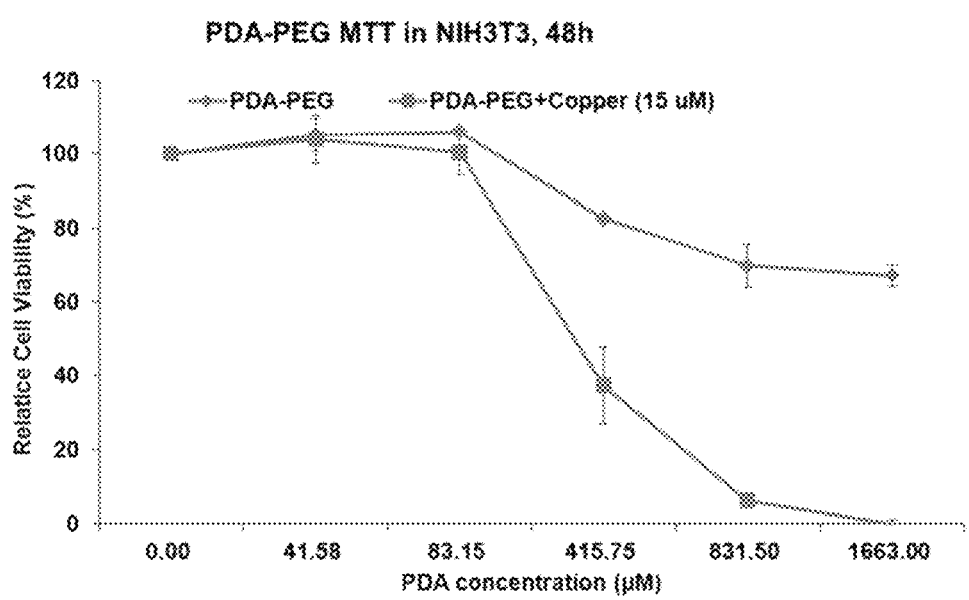
FIG. 18 demonstrates the cytotoxicity of disclosed material with NIH3T3 cells.
Figure 19:
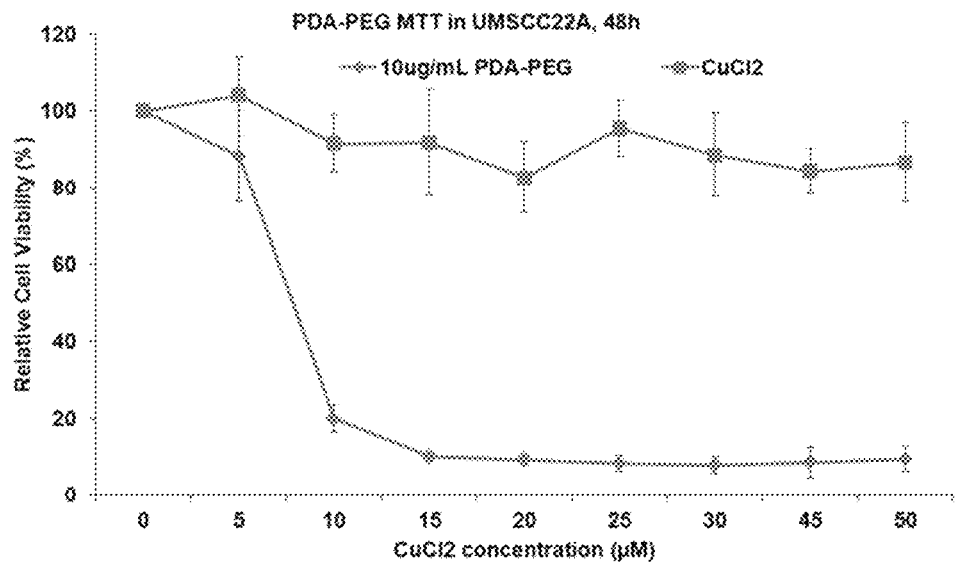
FIG. 19 demonstrates the cytotoxicity of disclosed material with UMSCC22A cells.
Figure 20:
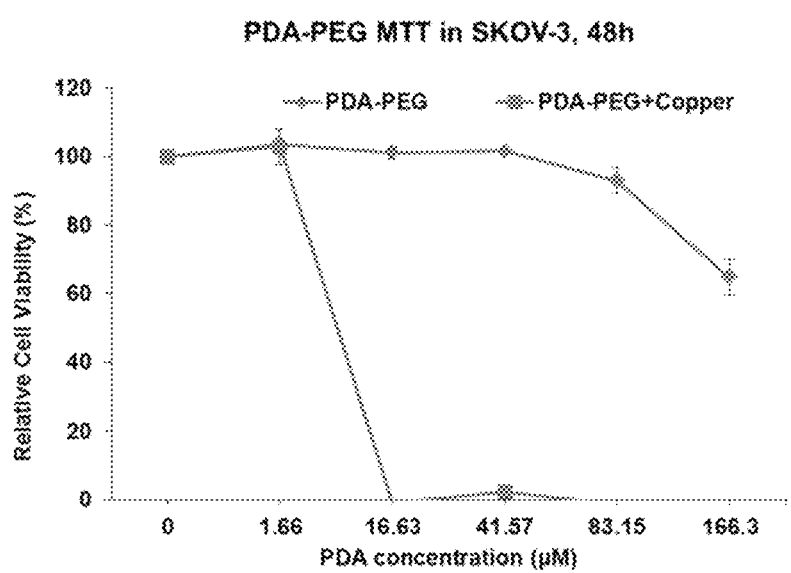
FIG. 20 demonstrates the cytotoxicity of disclosed material with SKOV-3 cells.
Figure 21:
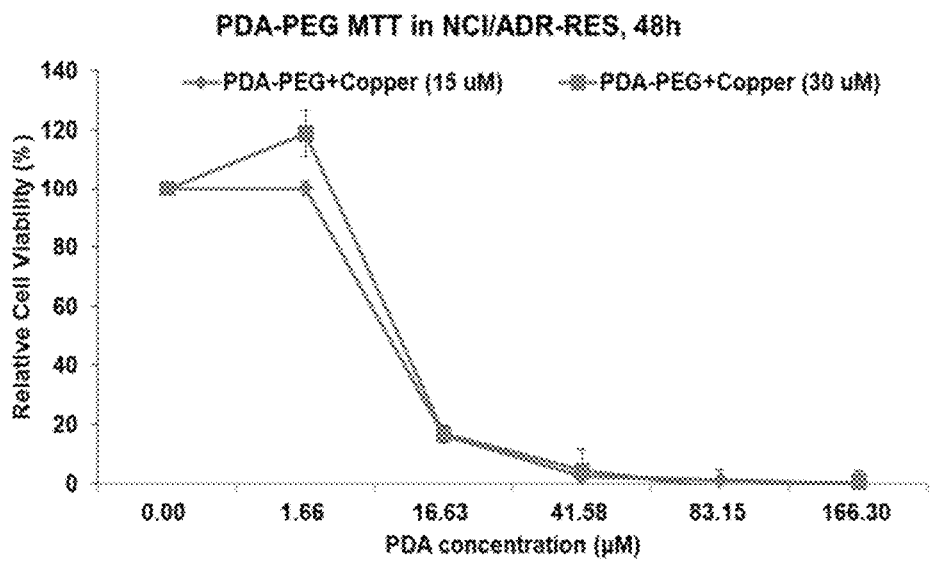
FIG. 21 demonstrates the cytotoxicity of disclosed material with NCI/ADR-Res cells.
Figure 22:
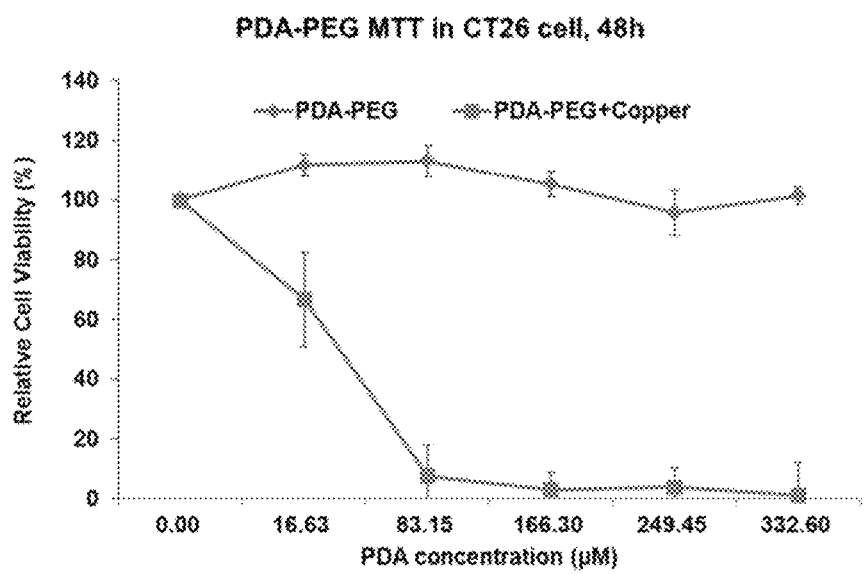
FIG. 22 demonstrates the cytotoxicity of disclosed material with CT26 cells.
Figure 23:
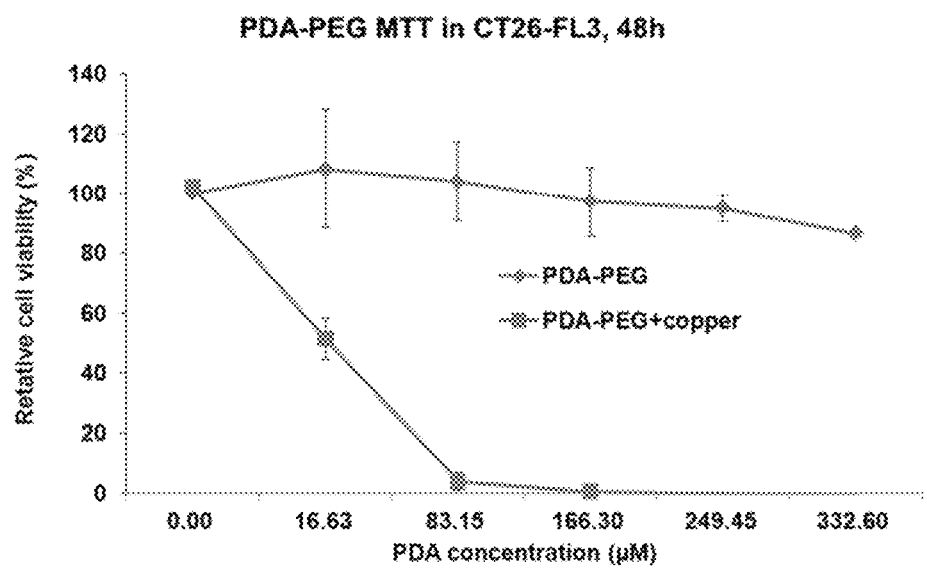
FIG. 23 demonstrates the cytotoxicity of disclosed material with CT26 FL3 cells.
Figure 24:
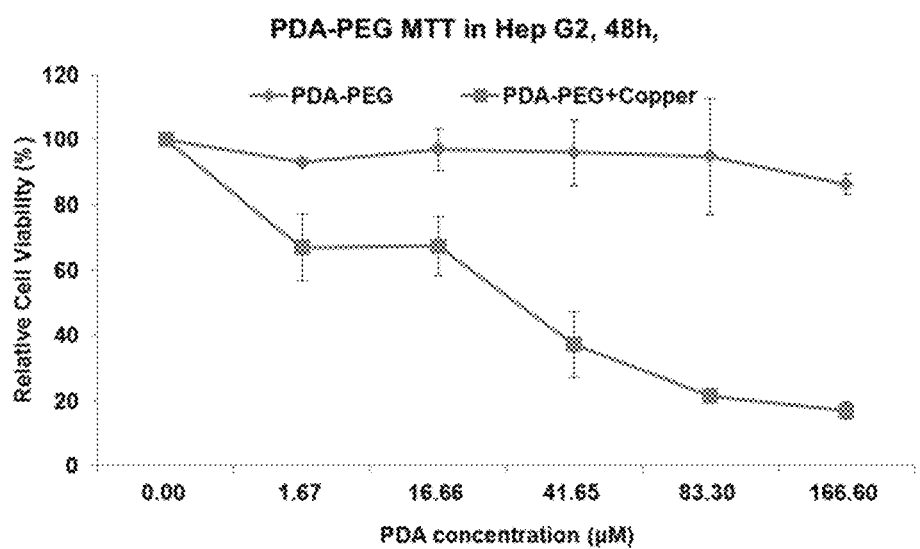
FIG. 24 demonstrates the cytotoxicity of disclosed material with Hep G2 cells.
Figure 25:
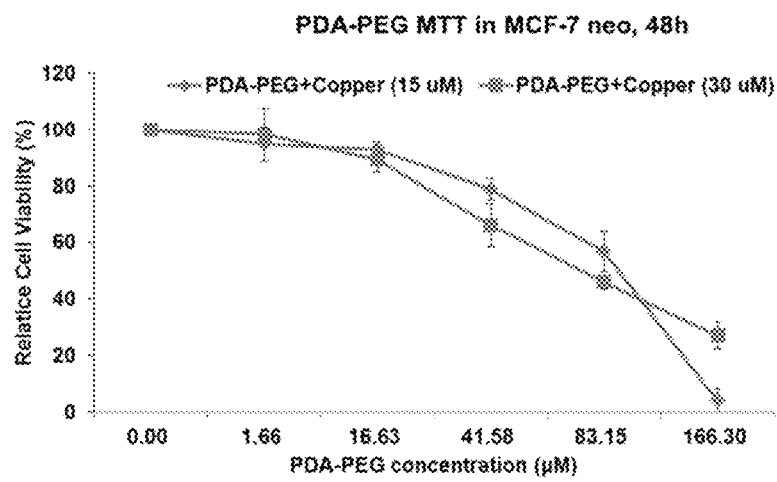
FIG. 25 demonstrates the cytotoxicity of disclosed material with MCF-7 neo cells.

Cytotoxicity of PDA-PEG and $CuCl_2$ combination for several cell types was determined including MCF10A-Her2 cells (FIG. 17), NIH3T3 cells (FIG. 18), UMSCC22A cells (FIG. 19), SKOV-3 cells (FIG. 20), NCI/ADR-Res cells (FIG. 21), CT26 cells (FIG. 22), CT26-FL3 cells (FIG. 23), Hep G2 cells (FIG. 24), and MCF-7 neo cells (FIG. 25).

Figure 26:
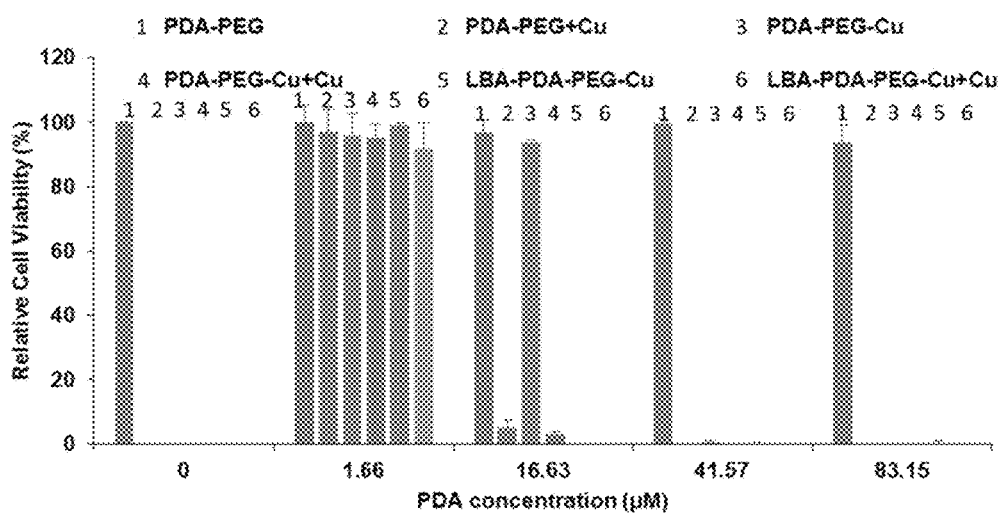
FIG. 26 presents the cytotoxicity of the materials at increasing concentration for SKOV-3 cells.
Figure 27:
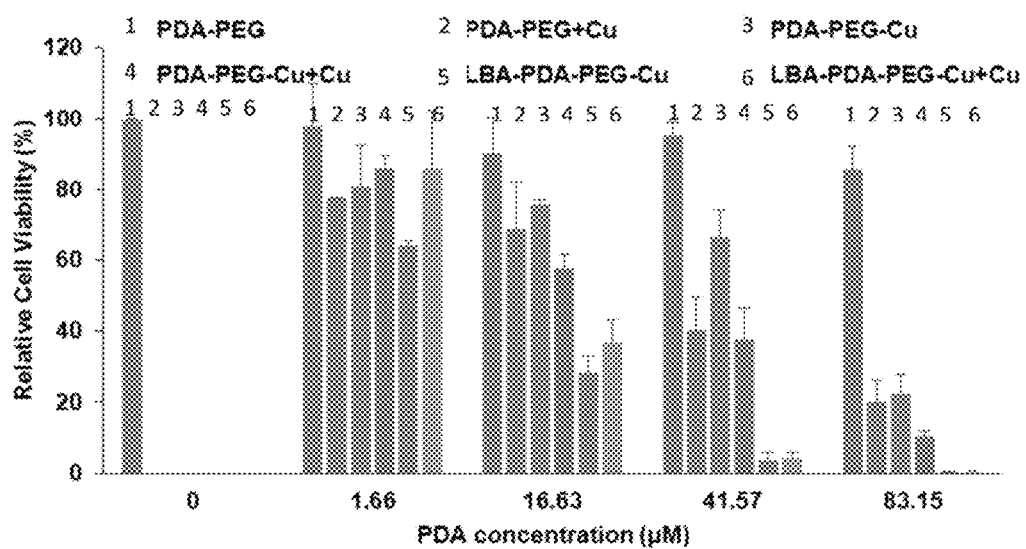
FIG. 27 presents the cytotoxicity of the materials at increasing concentration for HCT-116 cells.

Cytotoxicity of the materials at various concentrations for SKOV-3 cells is shown in FIG. 26 and Cytotoxicity of the materials at various concentrations for HCT-116 cells is shown in FIG. 27.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method for decreasing the viability of cancer cells, wherein the cancer cells comprises ovarian cancer cells, breast cancer cells, cervical cancer cells, prostate cancer cells, lung cancer cells, or white blood cells; the method comprising delivery of a polymer/copper combination to an environment comprising the cancer cells, the polymer/copper combination comprising a biocompatible copolymer, the biocompatible copolymer including pyridine-2-thiol groups pendant to a backbone of the copolymer via a disulfide linkage, the biocompatible copolymer comprising the reaction product of an acrylamide or acrylate-containing first reactant that includes a hydrophilic component with an acrylamide or acrylate-containing monomer that includes the pyridine-2-thiol groups, the polymer/copper combination being in the form of a self-assembled article comprising the hydrophilic component at the exterior surface of the particle, the polymer/copper combination further comprising copper ions complexed with the biocompatible copolymer via chelation of the copper ions with the pyridines of the pyridine-2-thiol groups.

2. The method of claim 1, wherein the environment comprises drug resistant cancer cells.

3. The method of claim 1, the biocompatible copolymer comprising hydrophilic groups of the first reactant pendant to the polymer backbone.

4. The method of claim 3, wherein the pendant hydrophilic groups comprise poly(ethylene glycol).

5. The method of claim 1, wherein the first reactant comprises poly(ethylene glycol) methacrylate.

6. The method of claim 1, wherein the acrylamide or acylate containing monomer that includes the pyridine-2-thiol groups comprises (pyridine-2-thiol)ethyl acrylate, (pyridine-2-thiol) ethyl methacrylate, ethyl (2-(pyridin-2- yldisulfanyl)ethyl) carbonate, N-(2-(pyridin-2-yldisulfanyl) ethyl) methacrylamide, or N-(2-(pyridin-2-yldisulfanyl) ethyl) acrylamide.

7. The method of claim 1, wherein the biocompatible copolymer comprises additional functional groups pendant to the backbone via a disulfide linkage.

8. The method of claim 1, wherein the hydrophilic component comprises poly(ethylene glycol), poly(N-isopropylacrylamide) (polyNIPAAm), poly(N-(2-hydroxypropyl) methacrylamide) (polyHPMA), poly(acrylic acid) (PAAc), poly(DL-lactic acid-co-glycolic acid) PLGA, or poly(L-histidine).

9. The method of claim 7, wherein the additional functional groups comprise a copper chelator.

10. The method of claim 9, wherein the copper chelator comprises polyhydroxy functionality.

* * * * *